US012611153B2

(12) United States Patent
Lenga et al.

(10) Patent No.: US 12,611,153 B2
(45) Date of Patent: Apr. 28, 2026

(54) SYSTEM, METHOD, AND COMPUTER PROGRAM PRODUCT FOR CONTRAST-ENHANCED RADIOLOGY USING MACHINE LEARNING

(71) Applicant: Bayer Aktiengesellschaft, Leverkusen (DE)

(72) Inventors: Matthias Lenga, Leverkusen (DE); Marvin Purtorab, Hannover (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 96 days.

(21) Appl. No.: 18/280,193

(22) PCT Filed: Nov. 29, 2021

(86) PCT No.: PCT/EP2021/083324
§ 371 (c)(1),
(2) Date: Sep. 1, 2023

(87) PCT Pub. No.: WO2022/184298
PCT Pub. Date: Sep. 9, 2022

(65) Prior Publication Data
US 2024/0050054 A1     Feb. 15, 2024

(30) Foreign Application Priority Data

Mar. 2, 2021     (EP) ..................................... 21160325
Apr. 7, 2021     (EP) ..................................... 21167116

(51) Int. Cl.
*A61B 6/00*          (2006.01)
*A61B 6/03*          (2006.01)
*A61B 8/00*          (2006.01)

(52) U.S. Cl.
CPC .............. *A61B 6/481* (2013.01); *A61B 6/032* (2013.01); *A61B 8/481* (2013.01)

(58) Field of Classification Search
CPC .. A61B 6/481; G06T 5/60; G06T 2207/10116
See application file for complete search history.

(56) References Cited

U.S. PATENT DOCUMENTS

2014/0376794 A1*  12/2014  Dumoulin et al. ..... G06T 11/00
2021/0241458 A1*   8/2021  Zaharchuk et al.
(Continued)

FOREIGN PATENT DOCUMENTS

EP          3714784 A1      9/2020
JP      2019-181226 A      10/2019
(Continued)

OTHER PUBLICATIONS

Maarten L Terpstra, "Deep learning-based image reconstruction and motion estimation from undersampled radial kspace for real-time MRI-guided radiotherapy", 2020, Phys. Med. Biol. 65, p. 1-13 (Year: 2020).*
(Continued)

*Primary Examiner* — Serkan Akar
*Assistant Examiner* — Kaitlyn Eunji Kim
(74) *Attorney, Agent, or Firm* — Morrison & Foerster LLP

(57)          ABSTRACT

A method for providing a prediction of a representation of an examination region that was generated using a medical image technique involving a contrast agent may include receiving a first representation in frequency space of an examination region of an examination object, receiving a second representation in the frequency space of the examination region of the examination object, providing the first representation and the second representation as an input to a predictive machine learning model that is configured to provide, as an output, a prediction of a representation in the frequency space of the examination region with an amount of the contrast agent administered during a medical imaging (Continued)

technique, receiving the output of the predictive machine learning model based on the input, and converting the output of the predictive machine learning model to a representation in real space of the examination region of the examination object.

8 Claims, 9 Drawing Sheets

(56)                References Cited

U.S. PATENT DOCUMENTS

| | | | |
|---|---|---|---|
| 2024/0050053 A1 | 2/2024 | Lenga et al. | |
| 2024/0153163 A1 | 5/2024 | Lenga et al. | |

FOREIGN PATENT DOCUMENTS

| | | |
|---|---|---|
| WO | 2018183044 A1 | 10/2018 |
| WO | 2018200493 A1 | 11/2018 |
| WO | 2019074938 A1 | 4/2019 |
| WO | 2019204406 A1 | 10/2019 |
| WO | 2019241659 A1 | 12/2019 |
| WO | 2022184297 A1 | 9/2022 |
| WO | 2022189015 A1 | 9/2022 |

OTHER PUBLICATIONS

Jan Menke, "Viewing the effective k-space coverage of MR images: phantom experiments with fast Fourier transform", 2010, Magnetic Resonance Imaging. 28, p. 1-8 (Year: 2010).*

3D Generative Adversarial Network, Learning a Probabilistic Latent Space of Object Shapes via 3D Generative—Adversarial Modeling, http://3dgan.csail.mit.edu/, 3 pages.

Abonyi, C.L. et al. (2016). "Intravascular Contrast Media in Radiography: Historical Development & Review of Risk Factors for Adverse Reactions," South American Journal of Clinical Research, vol. 3, Issue 1, 1-10.

ACR Manual on Contrast Media, 2020, ISBN: 978-1-55903-012-0.

Birkfellner, W. "Applied Medical Image Processing: A Basic Course", Verlag Taylor & Francis, 2014, Second Edition, ISBN: 9781466555570, 1-5.

Bracewell, R. (2004). "Fourier Analysis and Imaging," Verlag Springer Science & Business Media, 2004, ISBN: 9780306481871.

Burger, W. et al. (2016). Digital Image Processing An Algorithmic Introduction Using Java, Digital Image Processing, Texts in Computer Science, Second Edition, Springer-Verlag London 2016, 1-811.

Ignee, A. et al. (2016). Ultrasound contrast agents, Endosc Ultrasound. Nov.-Dec. 2016; 5(6): 355-362).

International Search Report (English translation) for PCT Application No. PCT/EP2021/083321, mailed on Mar. 14, 2022, 2 pages.

International Search Report (English translation) for PCT Application No. PCT/EP2021/083324, mailed on Mar. 15, 2022, 4 pages.

International Search Report (English translation) for PCT Application No. PCT/EP2021/083325, mailed on Mar. 11, 2022, 2 pages.

Jascinth, A. S. et al. (2016). "Contrast Agents in Computed Tomography: A Review," Journal of Applied Dental and Medical Sciences, vol. 2, Issue 2, 144-149.

Khan, S. et al. (2019). "A Guide to Convolutional Neural Networks for Computer Vision," Morgan & Claypool Publishers 2018, ISBN 1681730227, 9781681730226, 209 pages.

Lusic, H. et al. (2013). "X-Ray Computed Tomography Contrast Agents," Chem Rev. Mar. 13, 2013; 113(3), 1-64.

Nouh, M. R. et al. (2017). "Radiographic and magnetic resonances contrast agents: Essentials and tips for safe practices," World Journal of Radiology Sep. 28, 2017; 9(9): 339-349.

Perez, C. (2019). "Machine Learning Techniques: Supervised Learning and Classification. Examples with MATLAB," Amazon Digital Services LLC—Kdp Print US, 2019, ISBN 1096996545, 9781096996545.

Robbins, J. B. (2010) "Contrast Media Tutorial," https://www.radiology.wisc.edu/wp-content/uploads/2017/10/contrast-agents-tutorial.pdf, 1-32.

Song, H.K. et al., (2000). "k-Space Weighted Image Contrast (KWIC) for Contrast Manipulation in Projection Reconstruction MRI," Magnetic Resonance in Medicine 44:825-832.

* cited by examiner

100

200

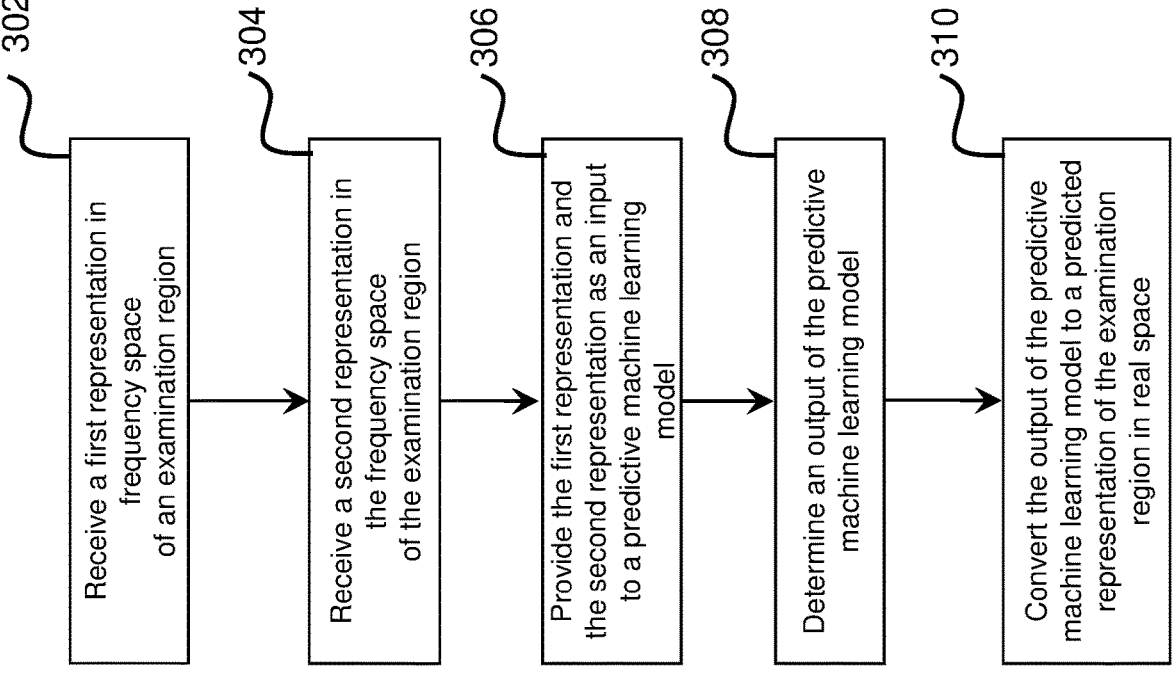

300

302 Receive a first representation in frequency space of an examination region

304 Receive a second representation in the frequency space of the examination region 306 Provide the first representation and the second representation as an input to a predictive machine learning model 308 Determine an output of the predictive machine learning model 310 Convert the output of the predictive machine learning model to a predicted representation of the examination region in real space

FIG. 3

400

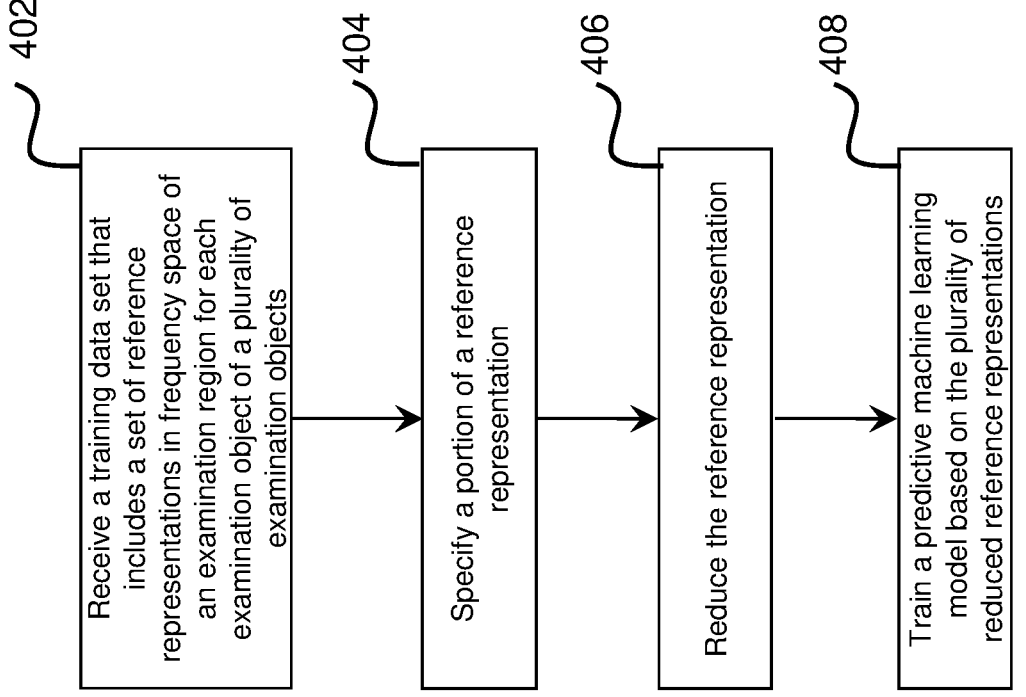

402

Receive a training data set that includes a set of reference representations in frequency space of an examination region for each examination object of a plurality of examination objects

404

Specify a portion of a reference representation

406

Reduce the reference representation

408

Train a predictive machine learning model based on the plurality of reduced reference representations

FIG. 4

SYSTEM, METHOD, AND COMPUTER PROGRAM PRODUCT FOR CONTRAST-ENHANCED RADIOLOGY USING MACHINE LEARNING

CROSS-REFERENCE TO RELATED APPLICATIONS

This application is a national stage application under 35 U.S.C. § 371 of International Application No. PCT/EP2021/083324, filed internationally on Nov. 29, 2021, which claims priority to European Application No. 21160325.3, filed on Mar. 2, 2021, and European Application No. 21167116.9, filed on Apr. 7, 2021, the entire content of each is hereby incorporated by reference in their entirety.

FIELD

This disclosure relates generally to the generation of radiological images and, in particular, to systems, methods, and computer program products that provide for generating a prediction of a representation of a radiological image that was generated using a medical image technique involving a contrast agent.

BACKGROUND

Radiology may refer to a branch of medicine that uses medical imaging technology to diagnose and treat disease. Radiology may involve the application of electromagnetic radiation and mechanical waves, such as during ultrasound procedures, to generate images for diagnostic, therapeutic, and/or scientific purposes. In some examples, ionizing radiation such as x-ray radiation, gamma radiation, and/or electrons may be used to generate images during medical imaging procedures. Radiology also includes other imaging methods, such as computed tomography (CT), positron emission tomography (PET), sonography, magnetic resonance imaging (MRI), also referred to as nuclear MRI (NMRI), and/or the like, even though these medical imaging techniques do not use ionizing radiation. In some instances, a contrast agent (e.g., a radiological contrast material, a radiocontrast agent, contrast media, etc.), and/or a flushing agent, such as saline, may be used in a medical imaging technique, such as in angiography, CT, ultrasound, MRI, and/or the like. A contrast agent may be used (e.g., injected into a bloodstream of a patient) for providing contrast enhancement to an image generated based on the medical imaging technique. For example, a contrast agent may include substances or a mixture of substances that improve the depiction of structures and/or functions of the body of a patient (e.g., a human patient or an animal patient) during a medical imaging technique.

A CT scan (e.g., a computed axial tomography (CAT) scan) may include a medical imaging technique used in radiology to get detailed images of the body noninvasively for diagnostic purposes. A CT scan may be carried out by a CT scanner. A CT scanner may use a rotating x-ray tube and a row of detectors placed in a gantry to measure X-ray attenuations by different tissues inside the body of a patient. The multiple X-ray measurements taken from different angles may be processed on a computer using reconstruction algorithms to produce tomographic (e.g., cross-sectional) images of a body.

MRI may include a medical imaging technique, which is used especially in medical diagnostics for depicting structure and function of tissues and/or organs in the body of a patient. In MRI, the magnetic moments of protons in an examination object are aligned in a basic magnetic field, with the result that there is a macroscopic magnetization along a longitudinal direction. The magnetic moments of in the examination object are then deflected from a resting position (e.g., a relaxation position) by irradiation with high-frequency (HF) pulses (e.g., by excitation with HF pulses of electromagnetic radiation). The return of the protons from the excited states to the resting positions, or magnetization dynamics, may then be detected as relaxation signals by one or more HF receiver coils of an MRI machine. For spatial encoding, rapidly switched magnetic gradient fields may be superimposed on the basic magnetic field. The relaxation signals are initially present as raw data (e.g., detected MRI data) in frequency space (e.g., frequency domain, spatial frequency space, Fourier space, Fourier depiction, etc.) and can be transformed by an inverse Fourier transform into real space (e.g., image space). In one example, during the use of native MRI, tissue contrasts may be created by different relaxation times (e.g., the spin—lattice relaxation time and the spin-spin relaxation time, referred to as $T_1$ and $T_2$) and/or proton density. The spin—lattice relaxation time may describe the transition of the longitudinal magnetization to its equilibrium magnetization state, where spin—lattice relaxation time is measured as the time taken to reach 63.21% of the equilibrium magnetization prior to the resonance excitation. The spin-spin relaxation time may describe, in an analogous manner, the transition of transverse magnetization to its equilibrium magnetization state.

During a CT imaging procedure, iodine-containing solutions may be used as contrast agents. During an MRI imaging procedure, superparamagnetic substances (e.g., iron oxide nanoparticles, superparamagnetic iron-platinum particles (SIPPs), etc.) and/or paramagnetic substances (e.g., gadolinium chelates, manganese chelates, etc.) may be used as contrast agents. In a sonography imaging procedure, a liquid containing gas-filled microbubbles may be used, where the liquid is administered intravenously. MRI contrast agents exert an effect by altering relaxation times of structures that take up contrast agents. A distinction can be made between two groups of substances: paramagnetic substances and superparamagnetic substances. Both groups of substances have unpaired electrons that induce a magnetic field around the individual atoms or molecules. Superparamagnetic contrast agents result in a predominant shortening of T2, whereas paramagnetic contrast agents mainly lead to a shortening of T1. The effect of the contrast agents may be indirect, since the contrast agent itself does not emit a signal, but instead, merely influences the intensity of signals in the vicinity of the contrast agent. An example of a superparamagnetic contrast agent is iron oxide nanoparticles (e.g., superparamagnetic iron oxide (SPIO)). Examples of paramagnetic contrast agents include gadolinium chelates, such as gadopentetate dimeglumine (e.g., Magnevist®), gadoteric acid (e.g., Dotarem®, Dotagita®, Cyclolux®), gadodiamide (e.g., Omniscan®), gadoteridol (e.g., ProHance®), and gadobutrol (e.g., Gadovist®).

SUMMARY

Accordingly, disclosed are systems, methods, and computer program products for providing a prediction of a representation of an examination region that was generated using a medical image technique involving a contrast agent.

In some non-limiting embodiments, a system may provide a prediction of a representation of an examination region that was generated using a medical image technique involving a contrast agent. The system may comprise at least one processor programmed or configured to receive a first representation in frequency space of an examination region of an examination object, wherein the first representation comprises a representation of the examination region without an amount of a contrast agent administered during a medical imaging technique or with a first amount of the contrast agent administered during the medical imaging technique, receive a second representation in the frequency space of the examination region of the examination object, wherein the second representation comprises a representation of the examination region with a second amount of the contrast agent administered during the medical imaging technique, wherein the second amount of the contrast agent is different from the first amount of the contrast agent, provide an input to a predictive machine learning model, wherein the input to the predictive machine learning model comprises at least a portion of the first representation and at least a portion of the second representation, wherein the predictive machine learning model comprises a trained machine learning model configured to provide, as an output, a prediction of a representation in the frequency space of the examination region with a third amount of the contrast agent administered during the medical imaging technique, wherein the third amount of the contrast agent is greater than the first amount of the contrast agent and the second amount of the contrast agent, receive the output of the predictive machine learning model based on the input, convert the output of the predictive machine learning model to a predicted representation in real space of the examination region of the examination object, and provide the predicted representation of the examination region of the examination object in the real space.

In some non-limiting embodiments, a computer program product may for provide a prediction of a representation of an examination region that was generated using a medical image technique involving a contrast agent. The computer program product may comprise at least one non-transitory computer-readable medium including one or more instructions that, when executed by at least one processor, cause the at least one processor to: receive a first representation in frequency space of an examination region of an examination object, wherein the first representation comprises a representation of the examination region without an amount of a contrast agent administered during a medical imaging technique or with a first amount of the contrast agent administered during the medical imaging technique, receive a second representation in the frequency space of the examination region of the examination object, wherein the second representation comprises a representation of the examination region with a second amount of the contrast agent administered during the medical imaging technique, wherein the second amount of the contrast agent is different from the first amount of the contrast agent, provide an input to a predictive machine learning model, wherein the input to the predictive machine learning model comprises at least a portion of the first representation and at least a portion of the second representation, wherein the predictive machine learning model comprises a trained machine learning model configured to provide, as an output, a prediction of a representation in the frequency space of the examination region with a third amount of the contrast agent administered during the medical imaging technique, wherein the third amount of the contrast agent is greater than the first amount of the contrast agent and the second amount of the contrast agent, receive the output of the predictive machine learning model based on the input, convert the output of the predictive machine learning model to a predicted representation in real space of the examination region of the examination, and provide the predicted representation in the real space of the examination region of the examination object.

In some non-limiting embodiments, a method a may provide prediction of a representation of an examination region that was generated using a medical image technique involving a contrast agent. The method may comprise receiving, with at least one processor, a first representation in frequency space of an examination region of an examination object, wherein the first representation comprises a representation of the examination region without an amount of a contrast agent administered during a medical imaging technique or with a first amount of the contrast agent administered during the medical imaging technique, receiving, with the at least one processor, a second representation in the frequency space of the examination region of the examination object, wherein the second representation comprises a representation of the examination region with a second amount of the contrast agent administered during the medical imaging technique, wherein the second amount of the contrast agent is different from the first amount of the contrast agent, providing, with the at least one processor, an input to a predictive machine learning model, wherein the input to the predictive machine learning model comprises at least a portion of the first representation and at least a portion of the second representation, wherein the predictive machine learning model comprises a trained machine learning model configured to provide, as an output, a prediction of a representation in the frequency space of the examination region with a third amount of the contrast agent administered during the medical imaging technique, wherein the third amount of the contrast agent is greater than the first amount of the contrast agent and the second amount of the contrast agent, receiving, with the at least one processor, the output of the predictive machine learning model based on the input, converting, with the at least one processor, the output of the predictive machine learning model to a predicted representation in real space of the examination region of the examination object, and providing, with the at least one processor, the predicted representation in the real space of the examination region of the examination object.

Further non-limiting embodiments are set forth below.

Embodiment 1: A system for providing a prediction of a representation of an examination region that was generated using a medical image technique involving a contrast agent, the system comprising at least one processor programmed or configured to: receive a first representation in frequency space of an examination region of an examination object, wherein the first representation comprises a representation of the examination region without an amount of a contrast agent administered during a medical imaging technique or with a first amount of the contrast agent administered during the medical imaging technique; receive a second representation in the frequency space of the examination region of the examination object, wherein the second representation comprises a representation of the examination region with a second amount of the contrast agent administered during the medical imaging technique, wherein the second amount of the contrast agent is different from the first amount of the contrast agent; provide an input to a predictive machine learning model, wherein the input to the predictive machine learning model comprises at least a portion of the first representation and at least a portion of the second representation, wherein the predictive machine learning model comprises a trained machine learning model configured to provide, as an output, a prediction of a representation in the frequency space of the examination region with a third amount of the contrast agent administered during the medical imaging technique, wherein the third amount of the contrast agent is greater than the first amount of the contrast agent and the second amount of the contrast agent; receive the output of the predictive machine learning model based on the input; convert the output of the predictive machine learning model to a predicted representation in real space of the examination region of the examination object; and provide the predicted representation in the real space of the examination region of the examination object.

Embodiment 2: The system of embodiment 1, wherein the at least one processor is further programmed or configured to: specify a portion of the first representation that includes a center of the frequency space, a portion of the second representation that includes a center of the frequency space, or a portion of the first representation and a portion of the second representation that each include a center of the frequency space, provide a reduced representation in the frequency space of the examination region of the examination object; wherein the input to the predictive machine learning model comprises the reduced representation in the frequency space of the examination region of the examination object; and wherein, when providing the input to the predictive machine learning model, the at least one processor is programmed or configured to: provide the reduced representation in the frequency space of the examination region of the examination object as the input to the predictive machine learning model.

Embodiment 3: The system of embodiment 2, wherein the at least one processor is further programmed or configured to: supplement the output of the predictive machine learning model with: a portion of the first representation that does not include the center of the frequency space and was not specified to provide the reduced representation in the frequency space of the examination region of the examination object, a portion of the second representation that does not include the center of the frequency space and was not specified to provide the reduced representation in the frequency space of the examination region of the examination object, or a portion of the first representation and a portion of the second representation, which each do not include the center of the frequency space and were not specified to provide the reduced representation in the frequency space of the examination region of the examination object, to provide a supplemented output of the predictive machine learning model; wherein, when converting the output of the predictive machine learning model to the predicted representation in the real space of the examination region of the examination object, the at least one processor is programmed or configured to: convert the supplemented output of the predictive machine learning model to the predicted representation in the real space of the examination region of the examination object.

Embodiment 4: The system of any of embodiments 1-3, wherein the first amount of contrast agent administered during the medical imaging technique is greater than zero, wherein the second amount of contrast agent administered during the medical imaging technique is greater than the first amount of contrast agent.

Embodiment 5: The system of any of embodiments 1-3, wherein the first amount of contrast agent administered during the medical imaging technique is zero, wherein the second amount of contrast agent administered during the medical imaging technique is greater than the first amount of contrast agent.

Embodiment 6: The system of any of embodiments 1-5, wherein the at least one processor is further programmed or configured to: generate the first representation in the frequency space of the examination region of the examination object with regard to a first result of a radiological examination; and generate the second representation in the frequency space of the examination region of the examination object with regard to a second result of the radiological examination.

Embodiment 7: The system of embodiment 6, wherein the radiological examination is a magnetic resonance imaging examination, a computed tomography examination, or an ultrasound examination.

Embodiment 8: The system of embodiment 6, wherein the radiological examination is a magnetic resonance imaging examination, wherein, when receiving the first representation in the frequency space of the examination region of the examination object in the frequency space, the at least one processor is programmed or configured to: receive first k-space data associated with the magnetic resonance imaging examination of the examination region of the examination object; and wherein, when receiving the second representation in the frequency space of the examination region of the examination object in the frequency space, the at least one processor is programmed or configured to: receive second k-space data associated with the magnetic resonance imaging examination of the examination region of the examination object.

Embodiment 9: The system of any of embodiments 1-7, wherein, when receiving the first representation in the frequency space of the examination region of the examination object in the frequency space, the at least one processor is programmed or configured to: receive a first representation in real space of an examination region of an examination object, wherein the first representation in real space comprises a representation of the examination region without an amount of a contrast agent administered during a medical imaging technique or with a first amount of the contrast agent administered during the medical imaging technique; convert the first representation in real space to the first representation in frequency space of the examination region of the examination object; wherein, when receiving the second representation in the frequency space of the examination region of the examination object in the frequency space, the at least one processor is programmed or configured to: receive a second representation in the real space of the examination region of the examination object, wherein the second representation in real space comprises a representation of the examination region with a second amount of the contrast agent administered during the medical imaging technique, wherein the second amount of the contrast agent is different from the first amount of the contrast agent; convert the first representation in real space to the first representation in frequency space of the examination region of the examination object.

Embodiment 10: The system of any of embodiments 1-9, wherein the at least one processor is further programmed or configured to: train the predictive machine learning model based on a training data set, wherein the training data set comprises: a set of reference representations in the frequency space of an examination region for each examination object of a plurality of examination objects, each set of reference representations of the examination region of an examination object comprises: a first reference representation in the frequency space of the examination region of the examination object; a second reference representation in the frequency space of the examination region of the examination object; and a third reference representation in the frequency space of the examination region of the examination object; and wherein the first reference representation comprises a reference representation in the frequency space of the examination region without an amount of a contrast agent administered during a medical imaging technique or with a first amount of the contrast agent administered during the medical imaging technique; wherein the second reference representation comprises a reference representation in the frequency space of the examination region with a second amount of the contrast agent administered during the medical imaging technique; wherein the third reference representation comprises a reference representation in the frequency space of the examination region with a third amount of the contrast agent administered during the medical imaging technique.

Embodiment 11: The system of embodiment 10, wherein, when training the predictive machine learning model, the at least one processor is programmed or configured to: minimize an amount of error provided by an error function, wherein the error function quantifies a deviation between a prediction of a representation in the frequency space of the examination region of the examination object with the third amount of the contrast agent administered during the medical imaging technique and the third reference representation in the frequency space of the examination region of the examination object.

Embodiment 12: The system of any of embodiments 1-11, wherein the at least one processor is further programmed or configured to: train the predictive machine learning model based on a training data set, wherein the training data set comprises: a set of reduced reference representations in the frequency space of an examination region for each examination object of a plurality of examination objects, each set of reduced reference representations of the examination region of an examination object comprises: a first reduced reference representation in the frequency space of the examination region of the examination object; a second reduced reference representation in the frequency space of the examination region of the examination object; and a third reduced reference representation in the frequency space of the examination region of the examination object; and wherein the first reduced reference representation comprises a reference representation of a portion of a first reference representation in the frequency space of the examination region that includes a center of the frequency space, wherein the first reference representation comprises a reference representation of the examination region without an amount of a contrast agent administered during a medical imaging technique or with a first amount of the contrast agent administered during the medical imaging technique; wherein the second reduced reference representation comprises a reference representation of a portion of a second reference representation in the frequency space of the examination region that includes a center of the frequency space, wherein the second reference representation comprises a reference representation of the examination region with a second amount of the contrast agent administered during the medical imaging technique; wherein the third reduced reference representation comprises a reference representation of a portion of a third reference representation in the frequency space of the examination region that includes a center of the frequency space, wherein the third reference representation comprises a reference representation of the examination region with a third amount of the contrast agent administered during the medical imaging technique.

Embodiment 13: The system of embodiment 12, wherein, when training the predictive machine learning model, the at least one processor is programmed or configured to: minimize an amount of error provided by an error function, wherein the error function quantifies a deviation between a prediction of a reduced representation in the frequency space of the examination region of the examination object with the third amount of the contrast agent administered during the medical imaging technique and the third reduced reference representation in the frequency space of the examination region of the examination object.

Embodiment 14: A computer program product for providing a prediction of a representation of an examination region that was generated using a medical image technique involving a contrast agent, the computer program product comprising at least one non-transitory computer-readable medium including one or more instructions that, when executed by at least one processor, cause the at least one processor to: receive a first representation in frequency space of an examination region of an examination object, wherein the first representation comprises a representation of the examination region without an amount of a contrast agent administered during a medical imaging technique or with a first amount of the contrast agent administered during the medical imaging technique; receive a second representation in the frequency space of the examination region of the examination object, wherein the second representation comprises a representation of the examination region with a second amount of the contrast agent administered during the medical imaging technique, wherein the second amount of the contrast agent is different from the first amount of the contrast agent; provide an input to a predictive machine learning model, wherein the input to the predictive machine learning model comprises at least a portion of the first representation and at least a portion of the second representation, wherein the predictive machine learning model comprises a trained machine learning model configured to provide, as an output, a prediction of a representation in the frequency space of the examination region with a third amount of the contrast agent administered during the medical imaging technique, wherein the third amount of the contrast agent is greater than the first amount of the contrast agent and the second amount of the contrast agent; receive the output of the predictive machine learning model based on the input; convert the output of the predictive machine learning model to a predicted representation in real space of the examination region of the examination; and provide the predicted representation in the real space of the examination region of the examination object.

Embodiment 15: The computer program product of embodiment 14, wherein the one or more instructions further cause the at least one processor to: specify a portion of the first representation that includes a center of the frequency space, a portion of the second representation that includes a center of the frequency space, or a portion of the first representation and a portion of the second representation that each include a center of the frequency space, provide a reduced representation in the frequency space of the examination region of the examination object; wherein the input to the predictive machine learning model comprises the reduced representation in the frequency space of the examination region of the examination object; and wherein the one or more instructions that cause the at least one processor to provide the input to the predictive machine learning model, cause the at least one processor to: provide the reduced representation in the frequency space of the examination region of the examination object as the input to the predictive machine learning model.

Embodiment 16: The computer program product of embodiment 15, wherein the one or more instructions further cause the at least one processor to: supplement the output of the predictive machine learning model with: a portion of the first representation that does not include the center of the frequency space and was not specified to provide the reduced representation in the frequency space of the examination region of the examination object, a portion of the second representation that does not include the center of the frequency space and was not specified to provide the reduced representation in the frequency space of the examination region of the examination object, or a portion of the first representation and a portion of the second representation, which each do not include the center of the frequency space and were not specified to provide the reduced representation in the frequency space of the examination region of the examination object; provide a supplemented output of the predictive machine learning model; wherein the one or more instructions that cause the at least one processor to convert the output of the predictive machine learning model to the predicted representation in the real space of the examination region of the examination object, cause the at least one processor to: convert the supplemented output of the predictive machine learning model to the predicted representation in real space of the examination region of the examination object.

Embodiment 17: The computer program product of any of embodiments 14-16, wherein the first amount of contrast agent administered during the medical imaging technique is greater than zero, wherein the second amount of contrast agent administered during the medical imaging technique is greater than the first amount of contrast agent.

Embodiment 18: The computer program product of any of embodiments 14-16, wherein the first amount of contrast agent administered during the medical imaging technique is zero, wherein the second amount of contrast agent administered during the medical imaging technique is greater than the first amount of contrast agent.

Embodiment 19: The computer program product of any of embodiments 14-18, wherein the one or more instructions further cause the at least one processor to: generate the first representation in the frequency space of the examination region of the examination object with regard to a first result of a radiological examination; and generate the second representation in the frequency space of the examination region of the examination object with regard to a second result of the radiological examination.

Embodiment 20: The computer program product of embodiment 19, wherein the radiological examination is a magnetic resonance imaging examination, a computed tomography examination, or an ultrasound examination.

Embodiment 21: The computer program product of embodiment 19, wherein the radiological examination is a magnetic resonance imaging examination, wherein the one or more instructions that cause the at least one processor to receive the first representation in the frequency space of the examination region of the examination object, cause the at least one processor to: receive first k-space data associated with the magnetic resonance imaging examination of the examination region of the examination object; and wherein the one or more instructions that cause the at least one processor to receive the second representation in the frequency space of the examination region of the examination object, cause the at least one processor to: receive second k-space data associated with the magnetic resonance imaging examination of the examination region of the examination object.

Embodiment 22: The computer program product of any of embodiments 14-20, wherein the one or more instructions that cause the at least one processor to receive the first representation in the frequency space of the examination region of the examination object, cause the at least one processor to: receive a first representation in real space of an examination region of an examination object, wherein the first representation in real space comprises a representation of the examination region without an amount of a contrast agent administered during a medical imaging technique or with a first amount of the contrast agent administered during the medical imaging technique; convert the first representation in real space to the first representation in frequency space of the examination region of the examination object; and wherein the one or more instructions that cause the at least one processor to receive the second representation in the frequency space of the examination region of the examination object, cause the at least one processor to: receive a second representation in the real space of the examination region of the examination object, wherein the second representation in real space comprises a representation of the examination region with a second amount of the contrast agent administered during the medical imaging technique, wherein the second amount of the contrast agent is different from the first amount of the contrast agent; convert the first representation in real space to the first representation in frequency space of the examination region of the examination object.

Embodiment 23: The computer program product of any of embodiments 14-22, wherein the one or more instructions further cause the at least one processor to: train the predictive machine learning model based on a training data set, wherein the training data set comprises: a set of reference representations in the frequency space of an examination region for each examination object of a plurality of examination objects, each set of reference representations of the examination region of an examination object comprises: a first reference representation in the frequency space of the examination region of the examination object; a second reference representation in the frequency space of the examination region of the examination object; and a third reference representation in the frequency space of the examination region of the examination object; and wherein the first reference representation in the frequency space comprises a reference representation of the examination region without an amount of a contrast agent administered during a medical imaging technique or with a first amount of the contrast agent administered during the medical imaging technique; wherein the second reference representation in the frequency space comprises a reference representation of the examination region with a second amount of the contrast agent administered during the medical imaging technique; wherein the third reference representation in the frequency space comprises a reference representation of the examination region with a third amount of the contrast agent administered during the medical imaging technique.

Embodiment 24: The computer program product of embodiment 23, wherein the one or more instructions that cause the at least one processor to train the predictive machine learning model, cause the at least one processor to: minimize an amount of error provided by an error function, wherein the error function quantifies a deviation between a prediction of a representation in the frequency space of the examination region of the examination object with the third amount of the contrast agent administered during the medical imaging technique and the third reference representation in the frequency space of the examination region of the examination object.

Embodiment 25: The computer program product of any of embodiments 14-24, wherein the one or more instructions further cause the at least one processor to: train the predictive machine learning model based on a training data set, wherein the training data set comprises: a set of reduced reference representations in the frequency space of an examination region for each examination object of a plurality of examination objects, each set of reduced reference representations of the examination region of an examination object comprises: a first reduced reference representation in the frequency space of the examination region of the examination object; a second reduced reference representation in the frequency space of the examination region of the examination object; and a third reduced reference representation in the frequency space of the examination region of the examination object; and wherein the first reduced reference representation comprises a reference representation of a portion of a first reference representation in the frequency space of the examination region that includes a center of the frequency space, wherein the first reference representation comprises a representation of the examination region without an amount of a contrast agent administered during a medical imaging technique or with a first amount of the contrast agent administered during the medical imaging technique; wherein the second reduced reference representation comprises a reference representation of a portion of a second reference representation in the frequency space of the examination region that includes a center of the frequency space, wherein the second reference representation comprises a reference representation of the examination region with a second amount of the contrast agent administered during the medical imaging technique; wherein the third reduced reference representation comprises a reference representation of a portion of a third reference representation in the frequency space of the examination region that includes a center of the frequency space, wherein the third reference representation comprises a reference representation of the examination region with a third amount of the contrast agent administered during the medical imaging technique.

Embodiment 26: The computer program product of embodiment 25, wherein the one or more instructions that cause the at least one processor to train the predictive machine learning model, cause the at least one processor to: minimize an amount of error provided by an error function, wherein the error function quantifies a deviation between a prediction of a reduced representation in the frequency space of the examination region of the examination object with the third amount of the contrast agent administered during the medical imaging technique and the third reduced reference representation in the frequency space of the examination region of the examination object.

Embodiment 27: A method for providing a prediction of a representation of an examination region that was generated using a medical image technique involving a contrast agent, comprising: receiving, with at least one processor, a first representation in frequency space of an examination region of an examination object, wherein the first representation comprises a representation of the examination region without an amount of a contrast agent administered during a medical imaging technique or with a first amount of the contrast agent administered during the medical imaging technique; receiving, with the at least one processor, a second representation in the frequency space of the examination region of the examination object, wherein the second representation comprises a representation of the examination region with a second amount of the contrast agent administered during the medical imaging technique, wherein the second amount of the contrast agent is different from the first amount of the contrast agent; providing, with the at least one processor, an input to a predictive machine learning model, wherein the input to the predictive machine learning model comprises at least a portion of the first representation and at least a portion of the second representation, wherein the predictive machine learning model comprises a trained machine learning model configured to provide, as an output, a prediction of a representation in the frequency space of the examination region with a third amount of the contrast agent administered during the medical imaging technique, wherein the third amount of the contrast agent is greater than the first amount of the contrast agent and the second amount of the contrast agent; receiving, with the at least one processor, the output of the predictive machine learning model based on the input; converting, with the at least one processor, the output of the predictive machine learning model to a predicted representation in real space of the examination region of the examination object; and providing, with the at least one processor, the predicted representation in the real space of the examination region of the examination object.

Embodiment 28: The method of embodiment 27, further comprising: specifying a portion of the first representation that includes a center of the frequency space, a portion of the second representation that includes a center of the frequency space, or a portion of the first representation and a portion of the second representation that each include a center of the frequency space, providing a reduced representation in the frequency space of the examination region of the examination object; wherein the input to the predictive machine learning model comprises the reduced representation in the frequency space of the examination region of the examination object; and wherein providing the input to the predictive machine learning model comprises: providing the reduced representation in the frequency space of the examination region of the examination object as the input to the predictive machine learning model.

Embodiment 29: The method of embodiment 28, further comprising: supplementing the output of the predictive machine learning model with: a portion of the first representation that does not include the center of the frequency space and was not specified to provide the reduced representation in the frequency space of the examination region of the examination object, a portion of the second representation that does not include the center of the frequency space and was not specified to provide the reduced representation in the frequency space of the examination region of the examination object, or a portion of the first representation and a portion of the second representation, which each do not include the center of the frequency space and were not specified to provide the reduced representation in the frequency space of the examination region of the examination object; providing a supplemented output of the predictive machine learning model; wherein converting the output of the predictive machine learning model to the representation in the real space of the examination region of the examination object comprises: converting the supplemented output of the predictive machine learning model to the representation in the real space of the examination region of the examination object.

Embodiment 30: The method of any of embodiments 27-29, wherein the first amount of contrast agent administered during the medical imaging technique is greater than zero, wherein the second amount of contrast agent administered during the medical imaging technique is greater than the first amount of contrast agent.

Embodiment 31: The method of any of embodiments 27-29, wherein the first amount of contrast agent administered during the medical imaging technique is zero, wherein the second amount of contrast agent administered during the medical imaging technique is greater than the first amount of contrast agent.

Embodiment 32: The method of any of embodiments 27-31, further comprising: generating the first representation in the frequency space of the examination region of the examination object with regard to a first result of a radiological examination; and generating the second representation in the frequency space of the examination region of the examination object with regard to a second result of the radiological examination.

Embodiment 33: The method of any of embodiment 32, wherein the radiological examination is a magnetic resonance imaging examination, a computed tomography examination, or an ultrasound examination.

Embodiment 34: The method of any of embodiment 32, wherein the radiological examination is a magnetic resonance imaging examination, wherein receiving the first representation in the frequency space of the examination region of the examination object comprises: receiving first k-space data associated with the magnetic resonance imaging examination of the examination region of the examination object; and wherein receiving the second representation in the frequency space of the examination region of the examination object comprises: receiving second k-space data associated with the magnetic resonance imaging examination of the examination region of the examination object.

Embodiment 35: The method of any of embodiments 27-33, wherein receiving the first representation in the frequency space of the examination region of the examination object comprises: receiving a first representation in real space of an examination region of an examination object, wherein the first representation in real space comprises a representation of the examination region without an amount of a contrast agent administered during a medical imaging technique or with a first amount of the contrast agent administered during the medical imaging technique; converting the first representation in real space to the first representation in frequency space of the examination region of the examination object; and wherein receiving the second representation in the frequency space of the examination region of the examination object comprises: receiving a second representation in the real space of the examination region of the examination object, wherein the second representation in real space comprises a representation of the examination region with a second amount of the contrast agent administered during the medical imaging technique, wherein the second amount of the contrast agent is different from the first amount of the contrast agent; converting the first representation in real space to the first representation in frequency space of the examination region of the examination object.

Embodiment 36: The method of any of embodiments 27-35, further comprising: training the predictive machine learning model based on a training data set, wherein the training data set comprises: a set of reference representations in the frequency space of an examination region for each examination object of a plurality of examination objects, each set of reference representations in the frequency space of the examination region of an examination object comprises: a first reference representation in the frequency space of the examination region of the examination object; a second reference representation in the frequency space of the examination region of the examination object; and a third reference representation in the frequency space of the examination region of the examination object; and wherein the first reference representation comprises a reference representation of the examination region without an amount of a contrast agent administered during a medical imaging technique or with a first amount of the contrast agent administered during the medical imaging technique; wherein the second reference representation comprises a reference representation of the examination region with a second amount of the contrast agent administered during the medical imaging technique; wherein the third reference representation comprises a reference representation of the examination region with a third amount of the contrast agent administered during the medical imaging technique.

Embodiment 37: The method of embodiment 36, wherein training the predictive machine learning model based comprises minimizing an amount of error provided by an error function, wherein the error function quantifies a deviation between a prediction of a representation in the frequency space of the examination region of the examination object with the third amount of the contrast agent administered during the medical imaging technique and the third reference representation in the frequency space of the examination region of the examination object.

Embodiment 38: The method of any of embodiments 27-37, further comprising: training the predictive machine learning model based on a training data set, wherein the training data set comprises: a set of reduced reference representations in the frequency space of an examination region for each examination object of a plurality of examination objects, each set of reduced reference representations in the frequency space of the examination region of an examination object comprises: a first reduced reference representation in the frequency space of the examination region of the examination object; a second reduced reference representation in the frequency space of the examination region of the examination object; and a third reduced reference representation in the frequency space of the examination region of the examination object; and wherein the first reduced reference representation comprises a reference representation of a portion of a first reference representation in the frequency space of the examination region that includes a center of the frequency space, wherein the first reference representation comprises a reference representation of the examination region without an amount of a contrast agent administered during a medical imaging technique or with a first amount of the contrast agent administered during the medical imaging technique; wherein the second reduced reference representation comprises a reference representation of a portion of a second reference representation in the frequency space of the examination region that includes a center of the frequency space, wherein the second reference representation comprises a reference representation of the examination region with a second amount of the contrast agent administered during the medical imaging technique; wherein the third reduced reference representation comprises a reference representation of a portion of a third reference representation in the frequency space of the examination region that includes a center of the frequency space, wherein the third reference representation comprises a reference representation of the examination region with a third amount of the contrast agent administered during the medical imaging technique.

Embodiment 39: The method of embodiment 38, wherein training the predictive machine learning model based comprises minimizing an amount of error provided by an error function, wherein the error function quantifies a deviation between a prediction of a reduced representation in the frequency space of the examination region of the examination object with the third amount of the contrast agent administered during the medical imaging technique and the third reduced reference representation in the frequency space of the examination region of the examination object.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present disclosure. As used in the specification and the claims, the singular form of "a," "an," and "the" include plural referents unless the context clearly dictates otherwise.

BRIEF DESCRIPTION OF THE DRAWINGS

Additional advantages and details of non-limiting embodiments are explained in greater detail below with reference to the exemplary embodiments that are illustrated in the accompanying schematic figures, in which:

FIG. 3 is a flowchart of a non-limiting embodiment of a process for providing a prediction of a representation of an examination region that was generated using a medical image technique involving a contrast agent;

FIG. 4 is a flowchart of a non-limiting embodiment of a process for training a predictive machine learning model to provide a prediction of a representation of an examination region;

DETAILED DESCRIPTION

Figure 1:
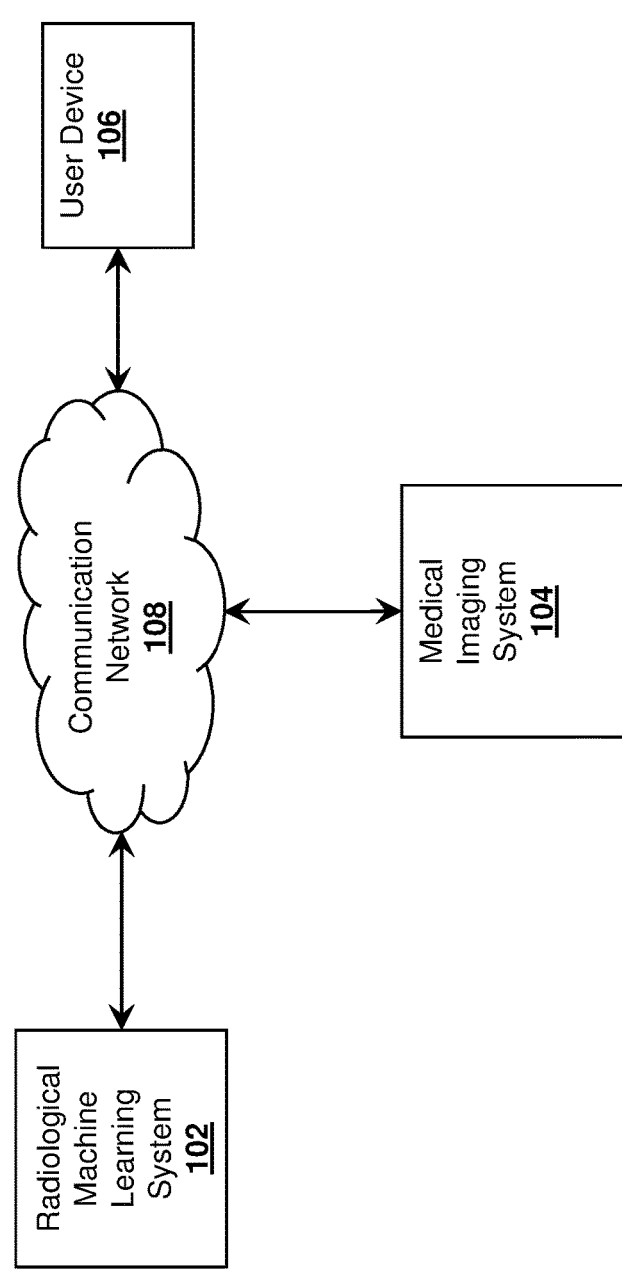
FIG. 1 is a diagram of a non-limiting embodiment of an environment in which systems, methods, and/or computer program products described herein may be implemented according to the present disclosure.

For purposes of the description hereinafter, the terms "end," "upper," "lower," "right," "left," "vertical," "horizontal," "top," "bottom," "lateral," "longitudinal," and derivatives thereof shall relate to the disclosure as it is oriented in the drawing figures. However, it is to be understood that the disclosure may assume various alternative variations and step sequences, except where expressly specified to the contrary. It is also to be understood that the specific devices and processes illustrated in the attached drawings, and described in the following specification, are simply exemplary embodiments or aspects of the disclosure. Hence, specific dimensions and other physical characteristics related to the embodiments or aspects of the embodiments, disclosed herein, are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." As used in the specification and the claims, the singular form of "a," "an," and "the" include plural referents, such as unless the context clearly dictates otherwise. Furthermore, as used herein, the terms "set" and "group" are intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise. Further, the phrase "based on" may mean "in response to" and be indicative of a condition for automatically triggering a specified operation of an electronic device (e.g., a controller, a processor, a computing device, etc.) as appropriately referred to herein.

As used herein, the term "system" may refer to one or more computing devices or combinations of computing devices such as, but not limited to, processors, servers, client devices, software applications, and/or other like components. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively send information to the second unit. As another example, a first unit may be in communication with a second unit if at least one intermediary unit (e.g., a third unit located between the first unit and the second unit) processes information received from the first unit and sends the processed information to the second unit. In some non-limiting embodiments, information may refer to a network packet (e.g., a data packet and/or the like) that includes data.

Some non-limiting embodiments are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

In some non-limiting embodiments, a machine learning model may be used as a way to reduce the amount of contrast agent used in the generation of radiological images. For example, during a first step in a process, a training data set may be generated. For a plurality of individuals (e.g., patients, persons, etc.), the training data set may include, for each individual, a native radiological image (e.g., a radiological image generated without an amount of a contrast agent administered during a medical imaging technique, such as a zero-contrast image, etc.), a low-contrast radiological image generated during the medical imaging technique based on (e.g., after) the administration of a low amount of contrast agent (e.g., a low-contrast image), and a full-contrast radiological image generated during the medical imaging technique based on the administration of a standard amount of contrast agent (e.g., a full-contrast image). In a second step, a machine learning model, such as an artificial neural network, may be trained to predict, for each individual included in the training data set, a predicted radiological image (e.g., an artificial radiological image), which shows an examination region after the administration of the standard amount of contrast agent, based on the native radiological image and the low-contrast radiological image. The full-contrast radiological image is used for each individual as a reference (e.g., ground truth) when training the predictive machine learning model. In a third step, the trained machine learning model can be used to predict for a new individual, on the basis of a native radiological image and of a low-contrast radiological image, a predicted radiological image which shows the examination region of the new individual as the examination region would look if a standard amount of contrast agent had been administered during the medical imaging technique. A similar process may be found in International Patent Application No. PCT/US2018/055034, filed on Oct. 9, 2018, which is incorporated by reference herein in its entirety.

However, during such a process, co-registration may be required to match individual radiological images of different individuals, such that the pixels/voxels correspond with one another. For example, co-registration of radiological images may be required so that an image element (e.g., a pixel or a voxel) of a radiological image of an examination region from an individual corresponds to (e.g., shows the same) an image element of another radiological image of the examination region from that individual. If the image elements of the radiological images do not correspond, artifacts may appear in the predicted radiological images, which can cover, distort, and/or simulate anatomical structures in the examination region.

In addition, the process described above may require the use of complete radiological images for training of the predictive machine learning model and generation of a predicted radiological image. For example, training of the predictive machine learning model and the generation of a predicted radiological image may require the use of complete radiological images after administration of varying amounts of contrast agent. In this way, the calculation complexity for generation of the predicted radiological image can increase rapidly. Additionally, a large amount of time may be required for calculations of the predicted radiological images, along with expensive hardware that may be required to carry out the calculations within a desired amount of time. Furthermore, the complete radiological images may need to be reduced in size, to partial regions (e.g., patches) and the partial regions may be required to be processed separately from one another in order not to overload the memory of the computer with overly large radiological images. However, such an approach can lead to artifacts at interfaces when the partial regions are processed separately from one another and are re-joined to form a complete radiological image (e.g., stitching artefacts). The subsequent removal of such stitching artifacts may require additional computational resources. Further, that approach may provide a risk of errors in the predicted radiological images that could be misinterpreted by a radiologist and could provide risk of misdiagnosis based on the complete radiological images.

Provided are improved systems, methods, and computer program products for providing a prediction of a representation of an examination region that was generated using a medical image technique involving a contrast agent. Embodiments of the present disclosure may include a system comprising at least one processor programmed or configured to: receive a first representation in frequency space of an examination region of an examination object, wherein the first representation comprises a representation of the examination region without an amount of a contrast agent administered during a medical imaging technique or with a first amount of the contrast agent administered during the medical imaging technique, receive a second representation in the frequency space of the examination region of the examination object, wherein the second representation comprises a representation of the examination region with a second amount of the contrast agent administered during the medical imaging technique, wherein the second amount of the contrast agent is different from the first amount of the contrast agent, provide an input to a predictive machine learning model, wherein the input to the predictive machine learning model comprises at least a portion of the first representation and at least a portion of the second representation, wherein the predictive machine learning model comprises a trained machine learning model configured to provide, as an output, a prediction of a representation in the frequency space of the examination region with a third amount of the contrast agent administered during the medical imaging technique, wherein the third amount of the contrast agent is greater than the first amount of the contrast agent and the second amount of the contrast agent, receive the output of the predictive machine learning model based on the input, convert the output of the predictive machine learning model to a predicted representation in real space of the examination region of the examination object, and provide the predicted representation of the examination region of the examination object in the real space.

In some non-limiting embodiments, the at least one processor is further programmed or configured to: specify a portion of the first representation that includes a center of the frequency space, a portion of the second representation that includes a center of the frequency space, or a portion of the first representation and a portion of the second representation that each include a center of the frequency space, provide a reduced representation in the frequency space of the examination region of the examination object, wherein the input to the predictive machine learning model comprises the reduced representation in the frequency space of the examination region of the examination object, and wherein, when providing the input to the predictive machine learning model, the at least one processor is programmed or configured to provide the reduced representation in the frequency space of the examination region of the examination object as the input to the predictive machine learning model. In some non-limiting embodiments, the at least one processor is further programmed or configured to: supplement the output of the predictive machine learning model with a portion of the first representation that does not include the center of the frequency space and was not selected to provide the reduced representation in the frequency space of the examination region of the examination object, a portion of the second representation that does not include the center of the frequency space and was not selected to provide the reduced representation in the frequency space of the examination region of the examination object, or a portion of the first representation and a portion of the second representation, which each do not include the center of the frequency space and were not selected to provide the reduced representation in the frequency space of the examination region of the examination object, provide a supplemented output of the predictive machine learning model, wherein, when converting the output of the predictive machine learning model to the predicted representation of the examination region of the examination object in the real space, the at least one processor is programmed or configured to convert the supplemented output of the predictive machine learning model to the predicted representation in the real space of the examination region of the examination object.

In some non-limiting embodiments, the first amount of contrast agent administered during the medical imaging technique is greater than zero, wherein the second amount of contrast agent administered during the medical imaging technique is greater than the first amount of contrast agent.

In some non-limiting embodiments, the first amount of contrast agent administered during the medical imaging technique is zero, wherein the second amount of contrast agent administered during the medical imaging technique is greater than the first amount of contrast agent (i.e., greater than zero).

In some non-limiting embodiments, the at least one processor is further programmed or configured to generate the first representation in the frequency space of the examination region of the examination object with regard to a first result of a radiological examination and generate the second representation in the frequency space of the examination region of the examination object with regard to a second result of the radiological examination. In some non-limiting embodiments, the radiological examination is a magnetic resonance imaging examination, a computed tomography examination, or an ultrasound examination.

In some non-limiting embodiments, when receiving the first representation in the frequency space of the examination region of the examination object in the frequency space, the at least one processor is programmed or configured to receive first k-space data associated with a magnetic resonance imaging (MRI) examination of the examination region of the examination object and wherein, when receiving the second representation in the frequency space of the examination region of the examination object in the frequency space, the at least one processor is programmed or configured to receive second k-space data associated with the MRI examination of the examination region of the examination object.

In some non-limiting embodiments, when receiving the first representation in the frequency space of the examination region of the examination object in the frequency space, the at least one processor is programmed or configured to: receive a first representation in real space of an examination region of an examination object, wherein the first representation in real space comprises a representation of the examination region without an amount of a contrast agent administered during a medical imaging technique or with a first amount of the contrast agent administered during the medical imaging technique; convert the first representation in real space to the first representation in frequency space of the examination region of the examination object; and wherein, when receiving the second representation in the frequency space of the examination region of the examination object in the frequency space, the at least one processor is programmed or configured to: receive a second representation in the real space of the examination region of the examination object, wherein the second representation in real space comprises a representation of the examination region with a second amount of the contrast agent administered during the medical imaging technique, wherein the second amount of the contrast agent is different from the first amount of the contrast agent; convert the first representation in real space to the first representation in frequency space of the examination region of the examination object.

In some non-limiting embodiments, the at least one processor is further programmed or configured to train the predictive machine learning model based on a training data set, wherein the training data set comprises a set of reference representations in the frequency space of an examination region for each examination object of a plurality of examination objects, each set of reference representations of the examination region of an examination object comprises a first reference representation in the frequency space of the examination region of the examination object, a second reference representation in the frequency space of the examination region of the examination object, and a third reference representation in the frequency space of the examination region of the examination object, and wherein the first reference representation comprises a reference representation of the examination region without an amount of a contrast agent administered during a medical imaging technique or with a first amount of the contrast agent administered during the medical imaging technique, wherein the second reference representation comprises a reference representation of the examination region with a second amount of the contrast agent administered during the medical imaging technique, and wherein the third reference representation comprises a reference representation of the examination region with a third amount of the contrast agent administered during the medical imaging technique.

In some non-limiting embodiments, when training the predictive machine learning model, the at least one processor is programmed or configured to minimize an amount of error provided by an error function, wherein the error function quantifies a deviation between a prediction of a representation in the frequency space of the examination region of the examination object with the third amount of the contrast agent administered during the medical imaging technique and the third reference representation in the frequency space of the examination region of the examination object.

In some non-limiting embodiments, the at least one processor is further programmed or configured to train the predictive machine learning model based on a training data set, wherein the training data set comprises a set of reduced reference representations in the frequency space of an examination region for each examination object of a plurality of examination objects, each set of reduced reference representations of the examination region of an examination object comprises a first reduced reference representation in the frequency space of the examination region of the examination object, a second reduced reference representation in the frequency space of the examination region of the examination object, and a third reduced reference representation in the frequency space of the examination region of the examination object, and wherein the first reduced reference representation comprises a reference representation of a portion of a first reference representation in the frequency space of the examination region that includes a center of the frequency space, wherein the first reference representation comprises a reference representation of the examination region without an amount of a contrast agent administered during a medical imaging technique or with a first amount of the contrast agent administered during the medical imaging technique, wherein the second reduced reference representation comprises a reference representation of a portion of a second reference representation in the frequency space of the examination region that includes a center of the frequency space, wherein the second reference representation comprises a reference representation of the examination region with a second amount of the contrast agent administered during the medical imaging technique, wherein the third reduced reference representation comprises a reference representation of a portion of a third reference representation in the frequency space of the examination region that includes a center of the frequency space, wherein the third reference representation comprises a reference representation of the examination region with a third amount of the contrast agent administered during the medical imaging technique.

In some non-limiting embodiments, when training the predictive machine learning model, the at least one processor is programmed or configured to minimize an amount of error provided by an error function, wherein the error function quantifies a deviation between a prediction of a reduced representation in the frequency space of the examination region of the examination object with the third amount of the contrast agent administered during the medical imaging technique and the third reduced reference representation in the frequency space of the examination region of the examination object.

In this way, the system may provide a predicted representation in real space of the examination region of the examination object that reduces use of a contrast agent to provide a representation in real space of the examination region of the examination object. Further, the system may provide a predicted representation in real space of the examination region of the examination object in a way that is tolerant with respect to errors in co-registration, such that a risk of artifacts, in particular stitching artifacts, may be avoided. Additionally, the system may require less computing resources for providing the predicted representation than a system that does not use a machine learning model configured to provide, as an output, a prediction of a representation in the frequency space of an examination region with a specific amount of the contrast agent administered during a medical imaging technique, and the system may allow for calculation complexity to be matched to a hardware configuration of the system. Furthermore, by using a reduced representation in the frequency space of an examination region of an examination object to provide the predicted representation in real space and/or by using a reduced reference representation in the frequency space of an examination region for an examination object to train the machine learning model, the system may reduce the amount of time required to provide the predicted representation in real space and/or to train the machine learning model as compared to a system that does not use a reduced representation in the frequency space of an examination region of an examination object to provide the predicted representation in real space or that does not use a reduced reference representation in the frequency space of an examination region for an examination object to train the machine learning model.

FIG. 1 provides a diagram of a non-limiting embodiment of an environment 100 in which devices, systems, methods, and/or computer program products, described herein, may be implemented. As shown in FIG. 1, environment 100 includes radiological machine learning system 102, medical imaging system 104, and user device 106. In some non-limiting embodiments, radiological machine learning system 102 may interconnect with (e.g., establish a connection to communicate with and/or the like) medical imaging system 104 and/or user device 106 via communication network 108. In some non-limiting embodiments, radiological machine learning system 102 may interconnect with medical imaging system 104, and user device 106 via wired connections, wireless connections, or a combination of wired and wireless connections.

Radiological machine learning system 102 may include one or more computing devices configured to communicate with medical imaging system 104 and/or user device 106 via communication network 108. For example, radiological machine learning system 102 may include a server, a group of servers, and/or other like devices. In some non-limiting embodiments, radiological machine learning system 102 may be a component of medical imaging system 104. In some non-limiting embodiments, radiological machine learning system 102 may include a cloud computing system.

Medical imaging system 104 may include one or more computing devices capable of being in communication with radiological machine learning system 102 and/or user device 106 via communication network 108. For example, medical imaging system 104 may include one or more scanners, such as a CT scanner and/or an MRI scanner, capable of communicating via communication network 108 and capable of performing medical imaging procedures involving the use of a contrast agent (e.g., a radiological contrast material).

User device 106 may include one or more computing devices configured to be in communication with radiological machine learning system 102 and/or medical imaging system 104 via communication network 108. For example, user device 106 may include a desktop computer (e.g., a client device that communicates with a server) and/or a portable computer, such as a laptop, a tablet, a smartphone, and/or the like. In some non-limiting embodiments or aspects, user device 106 may be associated with a user (e.g., an individual operating a device).

Communication network 108 may include one or more wired and/or wireless networks. For example, communication network 108 may include a cellular network (e.g., a long-term evolution (LTE) network, a third generation (3G) network, a fourth generation (4G) network, a fifth generation (5G) network, a code division multiple access (CDMA) network, and/or the like), a local area network (LAN), a wide area network (WAN), a wireless LAN (WLAN), a private network, an ad hoc network, an intranet, the Internet, a fiber optic-based network, an Ethernet network, a universal serial bus (USB) network, a cloud computing network, and/or the like, and/or a combination of some or all of these or other types of networks.

The number and arrangement of systems and/or devices shown in FIG. 1 are provided as an example. There may be additional systems and/or devices, fewer systems and/or devices, different systems and/or devices, or differently arranged systems and/or devices than those shown in FIG. 1. Furthermore, two or more systems and/or devices shown in FIG. 1 may be implemented within a single system or a single device, or a single system or a single device shown in FIG. 1 may be implemented as multiple, distributed systems or devices. Additionally or alternatively, a set of systems or a set of devices (e.g., one or more systems, one or more devices) of environment 100 may perform one or more functions described as being performed by another set of systems or another set of devices of environment 100.

Figure 2:
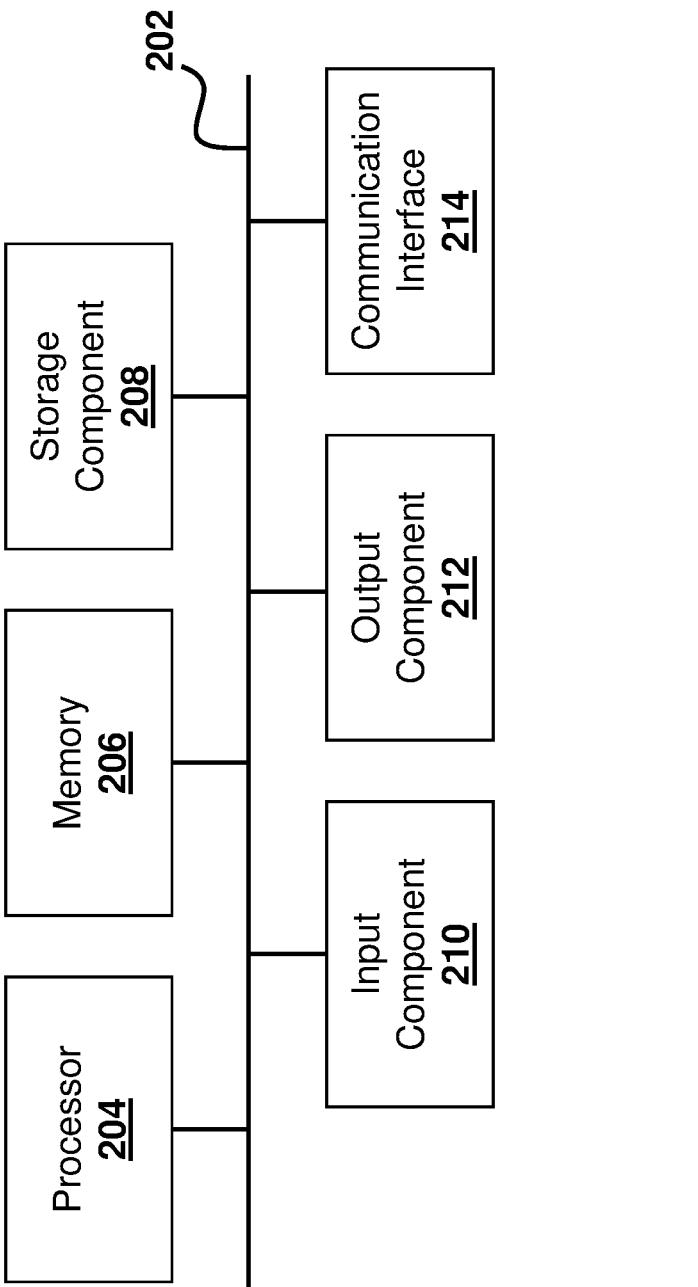
FIG. 2 is a diagram of a non-limiting embodiment of components of one or more devices and/or one or more systems of FIG. 1.

FIG. 2 depicts a diagram of example components of device 200. Device 200 may correspond to radiological machine learning system 102, medical imaging system 104, and/or user device 106. In some non-limiting embodiments, radiological machine learning system 102, medical imaging system 104, and/or user device 106 may include at least one device 200 and/or at least one component of device 200. As shown in FIG. 2, device 200 may include bus 202, processor 204, memory 206, storage component 208, input component 210, output component 212, and communication interface 214.

Bus 202 may include a component that permits communication among the components of device 200. In some non-limiting embodiments, processor 204 may be implemented in hardware, software, or a combination of hardware and software. For example, processor 204 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), and/or the like) that can be programmed to perform a function. Memory 206 may include random access memory (RAM), read-only memory (ROM), and/or another type of dynamic or static storage device (e.g., flash memory, magnetic memory, optical memory, and/or the like) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid-state disk, and/or the like), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touchscreen display, a keyboard, a keypad, a mouse, a button, a switch, a microphone, a camera, and/or the like). Additionally or alternatively, input component 210 may include a sensor for sensing information (e.g., a global positioning system (GPS) component, an accelerometer, a gyroscope, an actuator, and/or the like). Output component 212 may include a component that provides output information from device 200 (e.g., a display, a speaker, one or more light-emitting diodes (LEDs), and/or the like).

Communication interface 214 may include a transceiver-like component (e.g., a transceiver, a separate receiver and transmitter, and/or the like) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 200 may perform one or more processes described herein. Device 200 may perform these processes based on processor 204 executing software instructions stored on a computer-readable medium, such as memory 206 and/or storage component 208. A computer-readable medium (e.g., a non-transitory computer-readable medium) is defined herein as a non-transitory memory device. A non-transitory memory device may include memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database and/or the like). Device 200 may be capable of retrieving information from, storing information in, or searching information stored in the data storage or one or more data structures in memory 206 and/or storage component 208.

The number and arrangement of components shown in FIG. 2 are provided as an example. In some non-limiting embodiments, device 200 may include additional components, fewer components, different components, or differently arranged components than those shown in FIG. 2. Additionally or alternatively, a set of components (e.g., one or more components) of device 200 may perform one or more functions described herein as being performed by another set of components of device 200.

FIG. 3 provides a flowchart of a non-limiting embodiment of a process 300 for providing a prediction of a representation of an examination region that was generated using a medical image technique involving a contrast agent. In some non-limiting embodiments or aspects, one or more of the functions described with respect to process 300 may be performed (e.g., completely, partially, etc.) by radiological machine learning system 102. In some non-limiting embodiments or aspects, one or more of the steps of process 300 may be performed (e.g., completely, partially, and/or the like) by another device or a group of devices separate from and/or including radiological machine learning system 102, such as medical imaging system 104 and/or user device 106.

As shown in FIG. 3, at step 302, process 300 may include receiving a first representation in frequency space of an examination region. For example, radiological machine learning system 102 may receive the first representation in the frequency space of the examination region (e.g., the field of view (FOV), the image volume, etc.) in the frequency space from medical imaging system 104. In some non-limiting embodiments, radiological machine learning system 102 may receive the first representation in the frequency space of the examination region of an examination object from medical imaging system 104. In some non-limiting embodiments, the first representation may include a representation in the frequency space of the examination region without an amount of a contrast agent administered during a medical imaging technique (e.g., a medical imaging technique that would be performed during a radiological examination) or with a first amount of the contrast agent administered during the medical imaging technique. In some non-limiting embodiments, the first amount of the contrast agent administered during the medical imaging technique is greater than zero.

In some non-limiting embodiments, the examination object may include a living being, such as a mammal. In one example, the examination object may include a human being. In some non-limiting embodiments, the examination region may be part of the examination object that is subjected to a radiological examination (e.g., a radiological examination that involves a medical imaging technique). In one example, the examination region may include an organ or part of an organ of the examination object. In some non-limiting embodiments, the radiological examination may include a magnetic resonance imaging (MRI) examination, a computed tomography (CT) examination, and/or an ultrasound examination. In some non-limiting embodiments, the examination region may include a volume that is imaged in radiological images. The examination region may be defined by a radiologist (e.g., manually by a radiologist), for example on an overview image (localizer). Additionally or alternatively, the examination region may be defined automatically (e.g., automatically by radiological machine learning system 102, automatically by medical imaging system 104, etc.). For example, the examination region may be defined automatically based on a protocol (e.g., a specific protocol of medical imaging system 104).

In some non-limiting embodiments, the first representation in the frequency space of the examination region may include data associated with a radiological examination performed by medical imaging system 104. For example, the first representation in the frequency space of the examination region may include k-space data associated with an MRI examination (e.g., an MRI examination of the examination region of an examination object) performed by medical imaging system 104.

In some non-limiting embodiments, radiological machine learning system 102 may convert the first representation in the frequency space of the examination region to a first representation in real space (e.g., image space) of the examination region. For example, radiological machine learning system 102 may convert the first representation in the frequency space of the examination region to the first representation in real space of the examination region using an inverse Fourier transform.

In some non-limiting embodiments, radiological machine learning system 102 may generate the first representation in the frequency space of the examination region. For example, radiological machine learning system 102 may receive a first representation in real space of the examination region (e.g., a first radiological image of the examination region) and radiological machine learning system 102 may generate the first representation in the frequency space of the examination region based on the first representation in the real space of the examination region using a Fourier transform. In some non-limiting embodiments, radiological machine learning system 102 may receive the first representation in real space of the examination region as a two dimensional (2D) radiological image or a three dimensional radiological image of the examination region in real space and radiological machine learning system 102 may generate the first representation in the frequency space of the examination region based on the first representation in real space of the examination region using a 2D Fourier transform or a 3D Fourier transform, as appropriate.

As shown in FIG. 3, at step 304, process 300 may include receiving a second representation in the frequency space of the examination region. For example, radiological machine learning system 102 may receive the second representation in the frequency space of the examination region (e.g., the same examination region of the first representation) from medical imaging system 104. In some non-limiting embodiments, radiological machine learning system 102 may receive the second representation in the frequency space of the examination region of an examination object (e.g., the same examination object as the examination region of the first representation) from medical imaging system 104. In some non-limiting embodiments, the second representation may include a representation of the examination region with a second amount of the contrast agent administered during the medical imaging technique. In some non-limiting embodiments, the second amount of the contrast agent is different from the first amount of the contrast agent administered during the medical imaging technique that is associated with the first representation. In some non-limiting embodiments, the second amount of the contrast agent is greater than the first amount of the contrast agent administered during the medical imaging technique.

In some non-limiting embodiments, the second representation in the frequency space of the examination region may include data associated with a radiological examination performed by medical imaging system 104. For example, the second representation in the frequency space of the examination region may include k-space data associated with an MRI examination performed by medical imaging system 104.

In some non-limiting embodiments, radiological machine learning system 102 may receive k-space data associated with the first representation in the frequency space of the examination region and k-space data associated with the second representation in the frequency space of the examination region. For example, radiological machine learning system 102 may receive the first representation in the frequency space of the examination region as first k-space data associated with an MRI examination (e.g., first k-space data generated by an MRI examination) of the examination region and radiological machine learning system 102 may receive the second representation in the frequency space of the examination region as second k-space data associated with the MRI examination (e.g., second k-space data generated by the MRI examination) of the examination region. In some non-limiting embodiments, radiological machine learning system 102 may generate the first representation in the frequency space of the examination region with regard to first result of a radiological examination and radiological machine learning system 102 may generate the second representation in the frequency space of the examination region with regard to a second result of the radiological examination. For example, radiological machine learning system 102 may generate the first representation in the frequency space of the examination region based on k-space data associated with a first result of an MRI examination and radiological machine learning system 102 may generate the second representation in the frequency space of the examination region based on k-space data associated with a second result of the MRI examination. In some non-limiting embodiments, the first representation in the frequency space of the examination region may include first k-space data associated with an MRI examination of the examination region and/or the second representation in the frequency space of the examination region may include second k-space data associated with an MRI examination of the examination region.

In some non-limiting embodiments, radiological machine learning system 102 may convert the second representation in the frequency space of the examination region to a second representation in real space of the examination region. For example, radiological machine learning system 102 may convert the second representation in the frequency space of the examination region to the second representation in real space of the examination region using an inverse Fourier transform.

In some non-limiting embodiments, radiological machine learning system 102 may generate the second representation in the frequency space of the examination region. For example, radiological machine learning system 102 may receive a second representation in real space of the examination region (e.g., a first radiological image of the examination region) and radiological machine learning system 102 may generate the second representation in the frequency space of the examination region based on the second representation in the real space of the examination region using a Fourier transform. In some non-limiting embodiments, radiological machine learning system 102 may receive the second representation in real space of the examination region as a two dimensional (2D) radiological image or a three dimensional (3D) radiological image of the examination region and radiological machine learning system 102 may generate the second representation in the frequency space of the examination region based on the second representation in the real space of the examination region using a 2D Fourier transform or a 3D Fourier transform, as appropriate.

As shown in FIG. 3, at step 306, process 300 may include providing the first representation and the second representation as an input to a predictive machine learning model. For example, radiological machine learning system 102 may provide the input to the predictive machine learning model (e.g., a predictive algorithm, a prediction model, a predictive model, etc.), where the input to the predictive machine learning model includes at least a portion of the first representation in the frequency space of the examination region and at least a portion of the second representation in the frequency space of the examination region. In some non-limiting embodiments, the predictive machine learning model may include a trained machine learning model that is configured to provide, as an output, a prediction of a representation in the frequency space of the examination region of the examination object with a third amount of the contrast agent administered during a medical imaging technique (e.g., a medical imaging technique that is the same as the medical imaging technique associated with the first representation in the frequency space of the examination region and the second representation in the frequency space of the examination region). In some non-limiting embodiments, the prediction of the representation in the frequency space of the examination region with the third amount of the contrast agent administered during a medical imaging technique includes a prediction of the examination region of an examination object as the examination region would be represented if a specific amount of contrast agent (e.g., a standard amount of contrast agent that would be administered to the examination object based on parameters of the medical imaging technique and/or the examination object) had been administered to the examination region (e.g., the examination region of the examination object) without the specific amount actually having to be administered during the medical imaging technique.

In some non-limiting embodiments, the third amount of the contrast agent is different from the first amount of contrast agent and/or the second amount of contrast agent. For example, the third amount of the contrast agent may be greater than the first amount of the contrast agent administered during the medical imaging technique associated with the first representation in the frequency space of the examination region and greater than the second amount of the contrast agent administered during the medical imaging technique associated with the second representation in the frequency space of the examination region.

In some non-limiting embodiments, the predictive machine learning model may include an artificial neural network. In some non-limiting embodiments, the artificial neural network may include at least three layers of processing elements. For example, the artificial neural network may include a first layer with input neurons (e.g., nodes), an N-th layer with output neurons, and N−2 inner layers, where N is a natural number and greater than 2. In some non-limiting embodiments, the input neurons may be configured to receive the first representation in frequency space of an examination region of an examination object and the second representation in frequency space of the examination region of the examination object. The output neurons may be configured to provide (e.g., as an output) at least one prediction of a representation in the frequency space of the examination region with a specific amount of the contrast agent administered during a medical imaging technique, based on the input. In some non-limiting embodiments, processing elements of the layers between the input neurons and the output neurons are connected to one another in a predetermined pattern with predetermined connection weights. In some non-limiting embodiments, the connection weights may be updated during training of the machine learning model (e.g., training of the artificial neural network).

In some non-limiting embodiments, the predictive machine learning model may include a convolutional neural network (CNN). In some non-limiting embodiments, a CNN may be capable of processing an input in the form of a matrix. A CNN may include one or more filters (e.g., one or more convolutional layers) and one or more aggregation layers (e.g., one or more pooling layers), which may be repeated alternately and, the end of the CNN may include one or more layers of completely connected neurons (e.g., one or more dense/fully connected layers). Additionally or alternatively, the predictive machine learning model may include a generative adversarial network (GAN).

In some non-limiting embodiments, the input to the predictive machine learning model may further include information associated with an examination object (e.g., an examination object from which the examination region is obtained based on a radiological examination), information associated with an examination region (e.g., an examination region associated with the first representation and the second representation), and/or information associated with the radiological examination performed on the examination object (e.g., the examination region of the examination object). For example, the input to the predictive machine learning model may include information associated with the sex, age, weight, height, anamnesis, nature and duration and amount of medicaments already ingested, blood pressure, central venous pressure, breathing rate, serum albumin, total bilirubin, blood sugar, iron content, breathing capacity, and/or the like, of the examination object. Additionally or alternatively, the input to the predictive machine learning model may include pre-existing conditions of the examination region, medical operations associated with the examination region, such as a partial resection of the examination region, conditions of an organ, such as whether a liver transplantation took place, whether iron liver is present, whether fatty liver is present, and/or the like. Additionally or alternatively, the input to the predictive machine learning model may include a type of radiological examination performed on the examination object.

In some non-limiting embodiments, radiological machine learning system 102 may specify (e.g., select, choose, determine, etc.) a portion of (e.g., a region of) the first representation in the frequency space of the examination region that includes a center of the frequency space, a portion of the second representation in the frequency space of the examination region that includes a center of the frequency space, or a portion of the first representation in the frequency space of the examination region and a portion of the second representation in the frequency space of the examination region that each include a center of the frequency space, to provide a reduced representation in the frequency space of the examination region of the examination object. For example, radiological machine learning system 102 may automatically specify a portion of (e.g., a region of) the first representation in the frequency space of the examination region that includes a center of the frequency space, a portion of the second representation in the frequency space of the examination region that includes a center of the frequency space, or a portion of the first representation in the frequency space of the examination region and a portion of the second representation in the frequency space of the examination region that each include a center of the frequency space, to provide a reduced representation in the frequency space of the examination region of the examination object. In some non-limiting embodiments, radiological machine learning system 102 may specify a portion of a representation in the frequency space of the examination region (e.g., a portion of the first representation in the frequency space of the examination region, a portion of the second representation in the frequency space of the examination region, a portion of a reduced representation in the frequency space of the examination region, a portion of a reference representation in the frequency space of the examination region etc.) based on a manual input received from a user (e.g., a user of user device 106).

In one example, the reduced representation in the frequency space of the examination region of the examination object may include the portion of the first representation in the frequency space of the examination region that includes a center of the frequency space and the second representation in the frequency space of the examination region. In another example, the reduced representation in the frequency space of the examination region of the examination object may include the first representation in the frequency space of the examination region and the portion of the second representation in the frequency space of the examination region that includes a center of the frequency space. In yet another example, the reduced representation in the frequency space of the examination region of the examination object may include the portion of the first representation in the frequency space of the examination region that includes a center of the frequency space and the portion of the second representation in the frequency space of the examination region that includes the center of the frequency space.

In some non-limiting embodiments, the input to the predictive machine learning model comprises the reduced representation in the frequency space of the examination region of the examination object. In some non-limiting embodiments, radiological machine learning system 102 may provide the reduced representation in the frequency space of the examination region of the examination object as the input to the predictive machine learning model. By using a reduced representation in the frequency space of the examination region of the examination object, radiological machine learning system 102 may reduce computing resources requirements and calculation complexity that are used when obtaining an output of the predictive machine learning model based on the reduced representation in the frequency space of the examination region of the examination object.

The use of representations in frequency space of the examination region may have advantages over the use of representations in real space of the examination region. For example, co-registration of a representation is less critical in frequency space than in real space. Co-registration (e.g., image registration) may refer to a process in digital image processing that optimally matches (e.g., registers) two or more images of the same region or similar regions. One image may be defined as a reference image and the other image may be defined as an object image. The referenced image and the object image that are to be matched, may differ from one another because the referenced image and the object image were acquired from different positions, at different time points, and/or with different sensors. In order to optimally match an object image with a corresponding reference image, a compensating transformation may be calculated.

Representations in frequency space of the examination region may be more tolerant with respect to errors in co-registration during training, validation, and prediction procedures than representations in real space of the examination region. For example, if a representation in frequency space is superimposed with another representation in frequency with less accuracy, the lack of accuracy has less influence than if representations in real space of the examination region are superimposed with less accuracy. The reduced influence is due to the properties of the Fourier transform. For example, turns or rotations of representations in real space (e.g., images) may lead to image information (e.g. information associated with a visible structure) being localized in a different region of the image after the image is transformed using a Fourier transform. However, in the frequency space, such turns or rotations do not change the region in which the contrast information is provided since the contrast information of Fourier-transformed images (e.g., representations of images in frequency space) is mapped around the center of the frequency space.

A synonym for the term "center of the frequency space" is the term "origin of the frequency space". The center of the frequency space, e.g., corresponds to the point with the coordinates (0,0) in a two-dimensional cartesian coordinate system. Points that are close to the center of the frequency space represent lower frequencies than points that are further away from the center. Areas within the frequency space around the center contain more information about the contrast of a representation of an examination region than areas remote from the center.

A further advantage of the use of representations in frequency space of the examination region may be that contrast information is separated from detail information (e.g., fine structures). It is thus possible to concentrate, during a training procedure, on the contrast information to be learnt by the predictive machine learning model and to also concentrate, during a prediction procedure, on the contrast information that may be predicted by the predictive machine learning model. Whereas contrast information in a representation in real space of an examination region is usually distributed over an entire representation (e.g., each image element intrinsically bears information about contrast), the contrast information in a representation in frequency space of an examination region is encoded in and around the center of the frequency space. Accordingly, the low frequencies in a representation in frequency space of an examination region are responsible for the contrast information, whereas the high frequencies contain detail information about fine structures. Using of representations in frequency space of the examination region may make it possible to separate the contrast information, to limit training and prediction to the contrast information, and to re-introduce information about the fine structures after a training procedure and/or a prediction procedure.

As shown in FIG. 3, at step 308, process 300 may include determining an output of the predictive machine learning model. For example, radiological machine learning system 102 may provide the input to the predictive machine learning model and the predictive machine learning model may generate an output based on the input. Radiological machine learning system 102 may determine the output based on the predictive machine learning model generating the output. In some non-limiting embodiments, radiological machine learning system 102 may receive the output based on the predictive machine learning model generating the output. In some non-limiting embodiments, the output of the predictive machine learning model may include a third representation in the frequency space of the examination region, which may be the prediction of a representation (e.g., an artificial representation) in the frequency space of the examination region. In some non-limiting embodiments, the third representation may include a representation in the frequency space of the examination region with the third amount of the contrast agent administered during the medical imaging technique.

In some non-limiting embodiments, radiological machine learning system 102 may determine the output of the predictive machine learning model based on k-space data associated with an MRI examination of the examination region. For example, radiological machine learning system 102 may provide first k-space data associated with an MRI examination of the examination region and second k-space data associated with the MRI examination of the examination region as the input to the predictive machine learning model. Radiological machine learning system 102 may determine the output based on the predictive machine learning model generating the output using the first k-space data associated with an MRI examination of the examination region and second k-space data associated with the MRI examination of the examination region as the input.

As shown in FIG. 3, at step 310, process 300 may include converting the output of the predictive machine learning model to a predicted representation in real space of the examination region. For example, radiological machine learning system 102 may convert the output of the predictive machine learning model to a predicted representation in real space of the examination region (e.g., a prediction of a representation in real space of the examination region). In some non-limiting embodiments, the predicted representation in the real space of the examination region may include a predicted radiological image of the examination region (e.g., a prediction of a radiological image of the examination region) with the third amount of the contrast agent administered during a medical imaging technique (e.g., a medical imaging technique associated with the first representation in the frequency space of the examination region and the second representation in the frequency space of the examination region). In some non-limiting embodiments, radiological machine learning system 102 may convert the output of the predictive machine learning model to the predicted representation in real space of the examination region using an inverse Fourier transform.

In some non-limiting embodiments, radiological machine learning system 102 may perform an operation associated with the predicted representation in the real space of the examination region. For example, radiological machine learning system 102 may provide the predicted representation in the real space of the examination region as an output of radiological machine learning system 102. In such an example, radiological machine learning system 102 may provide (e.g., transmit) the predicted representation in the real space of the examination region to user device 106 and/or medical imaging system 104 (e.g., so that the predicted representation in the real space of the examination region may be output by user device 106 and/or medical imaging system 104). In some non-limiting embodiments, radiological machine learning system 102 may store the predicted representation in the real space of the examination region in a data structure associated with radiological machine learning system 102. In some non-limiting embodiments, radiological machine learning system 102 may display the predicted representation in the real space of the examination region on a display device.

In some non-limiting embodiments, radiological machine learning system 102 may supplement the output of the predictive machine learning model to provide a supplemented output of the predictive machine learning model. For example, radiological machine learning system 102 may supplement the output of the predictive machine learning model with a portion of the first representation in the frequency space of the examination region that does not include the center of the frequency space and was not specified to provide the reduced representation in the frequency space of the examination region of the examination object, a portion of the second representation in the frequency space of the examination region that does not include the center of the frequency space and was not specified to provide the reduced representation in the frequency space of the examination region of the examination object, or a portion of the first representation and a portion of the second representation, which each do not include the center of the frequency space and were not specified to provide the reduced representation in the frequency space of the examination region of the examination object, to provide the supplemented output of the predictive machine learning model. In some non-limiting embodiments, radiological machine learning system 102 may convert the supplemented output of the predictive machine learning model to the representation in the real space of the examination region of the examination object.

In some non-limiting embodiments, radiological machine learning system 102 may convert resultant signal strengths for various position coordinates of the predicted representation in the real space of the examination region into grey scale values and/or color values to provide a digital image in a common image format (e.g., a digital imaging and communications in medicine (DICOM) format).

FIG. 4 shows a flowchart of a non-limiting embodiment of a process 400 for training a predictive machine learning model that is configured to provide a prediction of a representation of an examination region with a specific amount of contrast agent administered during a medical imaging technique. In some non-limiting embodiments, the predictive machine learning model may be the same or similar to the predictive machine learning model as described with regard to process 300. In some non-limiting embodiments or aspects, one or more of the functions described with respect to process 400 may be performed (e.g., completely, partially, etc.) by radiological machine learning system 102. In some non-limiting embodiments or aspects, one or more of the steps of process 300 may be performed (e.g., completely, partially, and/or the like) by another device or a group of devices separate from and/or including radiological machine learning system 102, such as medical imaging system 104 and/or user device 106.

As shown in FIG. 4, at step 402, process 400 may include receiving a training data set that includes a set of reference representations in frequency space of an examination region for each examination object of a plurality of examination objects. In some non-limiting embodiments, radiological machine learning system 102 may receive the training data set, which includes a set of reference representations (e.g., a plurality of reference representations) in frequency space of an examination region for each examination object of a plurality of examination objects, from medical imaging system 104 and/or user device 106. In some non-limiting embodiments, radiological machine learning system 102 may retrieve the training data set from a data structure associated with radiological machine learning system 102. In some non-limiting embodiments, the examination region may be the same for all examination objects of the plurality of examination objects. In some non-limiting embodiments, a reference representation (e.g., a reduced reference representation) of an examination region may refer to a representation in the frequency space of the examination region that is used during a training process of the predictive machine learning model.

In some non-limiting embodiments, each reference representation in the frequency space of the examination region for each examination object may further include information associated with an examination object (e.g., an examination object from which the examination region is obtained based on a radiological examination), information associated with an examination region (e.g., an examination region associated with the first representation and the second representation), and/or information associated with the radiological examination performed on the examination object (e.g., the examination region of the examination object). For example, the information associated with the examination object may include information associated with the sex, age, weight, height, anamnesis, nature and/or duration/or and amount of medicaments already ingested, blood pressure, central venous pressure, breathing rate, serum albumin, total bilirubin, blood sugar, iron content, breathing capacity, and/or the like, of the examination object. Additionally or alternatively, the information associated with the examination region may include pre-existing conditions of the examination region, medical operations associated with the examination region, such as a partial resection of the examination region, conditions of an organ, such as whether a liver transplantation took place, whether iron liver is present, whether fatty liver is present, and/or the like. Additionally or alternatively, the information associated with the radiological examination performed on the examination object may include a type of radiological examination performed on the examination object.

In some non-limiting embodiments, the training data set may include a set (e.g., a plurality) of reference representations in frequency space of an examination region for each examination object of a plurality of examination objects. Each set of reference representations in frequency space of the examination region of the examination object may include a first reference representation in frequency space of the examination region of the examination object, a second reference representation in frequency space of the examination region of the examination object, and a third reference representation in frequency space of the examination region of the examination object. In some non-limiting embodiments, the first reference representation may include a reference representation in the frequency space of the examination region without an amount of a contrast agent administered during a medical imaging technique or with a first amount of the contrast agent administered during the medical imaging technique. In some non-limiting embodiments, the second reference representation may include a reference representation in the frequency space of the examination region with a second amount of the contrast agent administered during the medical imaging technique. In some non-limiting embodiments, the third reference representation may include a reference representation in the frequency space of the examination region with a third amount of the contrast agent administered during the medical imaging technique. In some non-limiting embodiments, the third amount of contrast agent may be a standard amount of contrast agent that would be administered to the examination object during the medical imaging technique based on parameters of the medical imaging technique and/or the examination object. In some non-limiting embodiments, the third reference representation may be a ground truth representation.

In some non-limiting embodiments, the first amount of the contrast agent administered during the medical imaging technique is greater than zero. In some non-limiting embodiments, the first amount of the contrast agent administered during the medical imaging technique is zero. In some non-limiting embodiments, the second amount of the contrast agent is different from the first amount of the contrast agent administered during the medical imaging technique that is associated with the first representation. In some non-limiting embodiments, the second amount of the contrast agent is greater than the first amount of the contrast agent administered during the medical imaging technique. In some non-limiting embodiments, the third amount of the contrast agent is different from the first amount of the contrast agent and/or from the second amount of the contrast agent. For example, the third amount of contrast agent may be greater than the first amount of the contrast agent administered during the medical imaging technique associated with the first representation in the frequency space of the examination region and greater than the second amount of the contrast agent administered during the medical imaging technique associated with the second representation in the frequency space of the examination region.

In some non-limiting embodiments, the training data set may include a set of reduced reference representations in frequency space of an examination region for each examination object of a plurality of examination objects. Each set of reduced reference representations in the frequency space of the examination region of an examination object may include a first reduced reference representation in the frequency space of the examination region of the examination object, a second reduced reference representation in the frequency space of the examination region of the examination object in the frequency space, and/or a third reduced reference representation in the frequency space of the examination region of the examination object. In some non-limiting embodiments, the first reduced reference representation may include a representation in the frequency space of a portion of a first reference representation in the frequency space of the examination region that includes a center of the frequency space. In some non-limiting embodiments, the second reduced reference representation may include a representation in the frequency space of a portion of a second reference representation in the frequency space of the examination region that includes the center of the frequency space. In some non-limiting embodiments, the third reduced reference representation may include a representation in the frequency space of a portion of a third reference representation in the frequency space of the examination region that includes the center of the frequency space.

As shown in FIG. 4, at step 404, process 400 may include specifying a portion of a reference representation. For example, radiological machine learning system 102 may specify a portion of (e.g., a region of) a reference representation (e.g., the same portion of each reference representation) of an examination region of an examination object that is used to provide a reduced reference representation in the frequency space of the examination region of the examination object. With this, radiological machine learning system 102 may provide a training data set that includes reduced reference representations in the frequency space of the examination region of an examination object of a plurality of examination objects.

In some non-limiting embodiments, radiological machine learning system 102 may specify (e.g., automatically specify) a portion (e.g., a specified portion) of each reference representation (e.g., each reference representation of a set of reference representations) in the frequency space of the examination region of an examination object of the plurality of examination objects to provide a reduced reference representation in the frequency space of the examination region of each examination object. For example, radiological machine learning system 102 may specify the portion of a reference representation in the frequency space of the examination region of a set of reference representations in the frequency space of the examination region so that the portion includes a center of frequency space. In some non-limiting embodiments, a center of the portion may correspond to the center of the frequency space. In some non-limiting embodiments, the portion may have a shape. For example, the specified portion may be round, angular, concave, and/or convex. In some non-limiting embodiments, the portion may be cube-shaped (e.g., cuboid) in the case of a 3D frequency space in a Cartesian coordinate system. In some non-limiting embodiments, the portion may be rectangular (e.g., square) in the case of a 2D frequency space in a Cartesian coordinate system. In some non-limiting embodiments, the specified portion may have the same dimension as the frequency space. For example, in the case of a 2D representation in a 2D frequency space, the portion may include a plane. In another example, in the case of a 3D representation in a 3D frequency space, the portion may include a volume.

As shown in FIG. 4, at step 406, process 400 may include reducing the reference representation. For example, radiological machine learning system 102 may reduce the reference representation in the frequency space of the examination region of the examination object based on the portion that was specified (e.g., the specified portion) to provide a reduced reference representation in the frequency space of the examination region of the examination object. In some non-limiting embodiments, radiological machine learning system 102 may reduce each reference representation by removing (e.g., discarding, cutting away, etc.) any part of a reference representation that does not lie in the portion of the reference representation. For example, radiological machine learning system 102 may reduce each reference representation by covering the reference representation with a mask (e.g., a mask that corresponds to the specified portion) and removing any part of the reference presentation that is not covered by the mask. In some non-limiting embodiments, when covering the reference representation with a mask, radiological machine learning system 102 may set one or more color values of an image element (e.g., a pixel, a voxel) that is not covered by the mask to zero (e.g., black).

As shown in FIG. 4, at step 408, process 400 may include training a predictive machine learning model using the plurality of reduced reference representations. For example, radiological machine learning system 102 may train a predictive machine learning model based on the plurality of reduced reference representations in the frequency space of an examination region (e.g., an examination region of an examination object). In some non-limiting embodiments, radiological machine learning system 102 may train a predictive machine learning model using a self-learning algorithm in a supervised machine learning process. In some non-limiting embodiments, radiological machine learning system 102 may use the self-learning algorithm to generate, during machine learning, a statistical model which is based on the training data set.

In some non-limiting embodiments, radiological machine learning system 102 may, during training, minimize an amount of error provided by an error function. In some non-limiting embodiments, the error function may quantify a deviation between a prediction of a representation (e.g., a predicted representation) of the examination region of the examination object with a specific amount of the contrast agent administered during the medical imaging technique and a ground truth reference representation in the frequency space of the examination region of the examination object (e.g., a ground truth reference representation in the frequency space of the examination region of the examination object with the specific amount of the contrast agent administered during the medical imaging technique). In some non-limiting embodiments, the error function quantifies a deviation between a prediction of a reduced representation (e.g., a predicted reduced representation) of the examination region of the examination object with the specific amount of the contrast agent administered during the medical imaging technique and a ground truth reduced reference representation in the frequency space of the examination region of the examination object.

In some non-limiting embodiments, the predictive machine learning model may be configured to provide, as an output, a prediction of a representation in the frequency space of the examination region with a specific amount of the contrast agent administered during a medical imaging technique (e.g., a medical imaging technique that is the same as the medical imaging technique associated with the first representation in the frequency space of the examination region and the second representation in the frequency space of the examination region). In some non-limiting embodiments, the specific amount of the contrast agent is different from a first amount of the contrast agent administered during the medical imaging technique associated with the first representation in the frequency space of the examination region and different from a second amount of the contrast agent administered during the medical imaging technique associated with a second representation in the frequency space of the examination region. For example, the specific amount of contrast agent is greater than a first amount of the contrast agent administered during the medical imaging technique associated with the first representation in the frequency space of the examination region and greater than a second amount of the contrast agent administered during the medical imaging technique associated with the second representation in the frequency space of the examination region.

In some non-limiting embodiments, radiological machine learning system 102 may train the predictive machine learning model based on k-space data. For example, each reduced reference representation in the frequency space of the examination region of an examination object may include k-space data associated with an MRI examination (e.g., an MRI examination performed by medical imaging system 104). Radiological machine learning system 102 may train the predictive machine learning model based on the k-space data included in each reduced reference representation in the frequency space of the examination region of the examination object for the plurality of examination objects.

In some non-limiting embodiments, radiological machine learning system 102 may train the predictive machine learning model using a backpropagation method. In this way, radiological machine learning system 102 may train the predictive machine learning model to have maximum reliability with regard to mapping of an input to a corresponding output. The mapping quality may be described by an error function (e.g., a loss function). During the backpropagation method, a goal is to minimize the error function. In the case of the backpropagation method, the predictive machine learning model may update (e.g., learn, be taught, etc.) by alteration of connection weights of nodes. In a trained state, the connection weights between the processing elements of the predictive machine learning model may contain information regarding a relationship between a first reference representation in the frequency space of an examination region and a second reference representation in the frequency space of an examination region and information regarding a third reference representation. The information may be used to predict a representation in the frequency space of the examination on the basis of the first and the second representation. In some non-limiting embodiments, radiological machine learning system 102 may use a cross-validation method to divide data into training and validation data sets. The training data set may be used in the backpropagation training of connection weights of nodes. The validation data set may be used to check the accuracy of a prediction of a representation provided by the trained predictive machine learning model based on data not used during training.

In some non-limiting embodiments, radiological machine learning system 102 may generate the predictive machine learning model based on the training data set. For example, radiological machine learning system 102 may generate the predictive machine learning model to perform a prediction of a representation (e.g., a representation in frequency space) of an examination region with a specific amount of contrast agent administered during a medical imaging technique (e.g., a medical imaging technique performed during a radiological examination).

In some non-limiting embodiments, the predictive machine learning model may include a machine learning model designed to receive, as an input, data associated with representations in the frequency space of an examination region with an amount (e.g., some amount, no amount, etc.) of a contrast agent administered during a medical imaging technique, and provide, as an output, a prediction of a representation in the frequency space of the examination region with a specific amount of the contrast agent administered during the medical imaging technique. For example, the predictive machine learning model may be designed to receive data associated with a first representation in frequency space of an examination region that comprises a representation of the examination region without an amount of a contrast agent administered during a medical imaging technique or with a first amount of the contrast agent administered during the medical imaging technique and data associated with a second representation in frequency space of an examination region that comprises a representation of the examination region with a second amount of the contrast agent administered during the medical imaging technique, and provide an output that includes a prediction of a representation in the frequency space of the examination region with a third amount of the contrast agent administered during the medical imaging technique. In some non-limiting embodiments, radiological machine learning system 102 may store the predictive machine learning model (e.g., for later use).

In some non-limiting embodiments, as described herein, radiological machine learning system 102 may process data associated with representations in frequency space of an examination region of an examination object to obtain training data (e.g., a training data set) for the predictive machine learning model. For example, radiological machine learning system 102 may process the data to change the data into a format that may be analyzed (e.g., by radiological machine learning system 102) to generate the predictive machine learning model. The data that is changed (e.g., the data that results from the change) may be referred to as training data. In some non-limiting embodiments, radiological machine learning system 102 may process the data associated with representations in the frequency space of an examination region of an examination object during a time interval to obtain the training data based on receiving the data. Additionally or alternatively, radiological machine learning system 102 may process the data to obtain the training data based on radiological machine learning system 102 receiving an indication, from a user (e.g., a user associated with user device 106) of radiological machine learning system 102, that radiological machine learning system 102 is to process the data, such as when radiological machine learning system 102 receives an indication to generate a predictive machine learning model for a time interval corresponding to the data.

In some non-limiting embodiments, radiological machine learning system 102 may process data associated with representations in frequency space of an examination region of an examination object by determining a predictive variable based on the data. A predictive variable may include a metric, associated with an examination region or an examination object, which may be derived based on the data associated with representation in frequency space of an examination region of an examination object. The predictive variable may be analyzed to generate a predictive machine learning model. For example, the predictive variable may include a variable associated with an examination object, such as a variable associated with the sex, age, weight, height, anamnesis, nature and/or duration and/or amount of medicaments already ingested, blood pressure, central venous pressure, breathing rate, serum albumin, total bilirubin, blood sugar, iron content, breathing capacity, and/or the like, of the examination object. Additionally or alternatively, the predictive variable may include a variable associated with an examination region, such as a variable associated with pre-existing conditions of the examination region, medical operations associated with the examination region, such as partial resection of the examination region, conditions of an organ, such as whether a liver transplantation took place, whether iron liver is present, whether fatty liver is present, and/or the like. Additionally or alternatively, the predictive variable may include a variable associated with the radiological examination performed on the examination object, such as a variable associated with a type of radiological examination performed on the examination object, and/or the like.

In some non-limiting embodiments, radiological machine learning system 102 may analyze the training data to generate the predictive machine learning model. For example, radiological machine learning system 102 may use machine learning techniques to analyze the training data to generate the predictive machine learning model. In some non-limiting embodiments, generating the predictive machine learning model (e.g., based on training data obtained from historical data associated with representations in the frequency space and/or real space of an examination region of an examination object) may be referred to as training the predictive machine learning model. The machine learning techniques may include, for example, supervised and/or unsupervised techniques, such as decision trees, random forests, logistic regressions, linear regression, gradient boosting, support-vector machines, extra-trees (e.g., an extension of random forests), Bayesian statistics, learning automata, Hidden Markov Modeling, linear classifiers, quadratic classifiers, association rule learning, and/or the like. In some non-limiting embodiments, the predictive machine learning model may include a model that is specific to a particular characteristic, for example, a model that is specific to a particular examination region, a particular examination object, a particular amount of a contrast agent that is administered during a medical imaging technique, and/or the like. Additionally or alternatively, the predictive machine learning model may be specific to a particular type of examination object (e.g., a type of mammal, such as a human being) that includes a specific type of examination region. In some non-limiting embodiments, radiological machine learning system 102 may generate one or more predictive machine learning models for one or more entities, a particular group of entities, and/or one or more users of one or more entities.

Additionally or alternatively, when analyzing the training data, radiological machine learning system 102 may identify one or more variables (e.g., one or more independent variables) as predictor variables (e.g., features) that may be used to make a prediction when analyzing the training data. In some non-limiting embodiments, values of the predictor variables may be inputs to the predictive machine learning model. For example, radiological machine learning system 102 may identify a subset (e.g., a proper subset) of the variables as the predictor variables that may be used to accurately predict a representation in the frequency space of an examination region. In some non-limiting embodiments, the predictor variables may include one or more of the examination region and/or examination object variables, as discussed above, that have a significant impact (e.g., an impact satisfying a threshold) on a prediction of a representation in the frequency space of an examination region with a specific amount of the contrast agent administered during a medical imaging technique as determined by radiological machine learning system 102.

In some non-limiting embodiments, radiological machine learning system 102 may validate the predictive machine learning model. For example, radiological machine learning system 102 may validate the predictive machine learning model after radiological machine learning system 102 generates the predictive machine learning model. In some non-limiting embodiments, radiological machine learning system 102 may validate the predictive machine learning model based on a portion of the training data to be used for validation. For example, radiological machine learning system 102 may partition the training data into a first portion and a second portion, where the first portion may be used to generate the predictive machine learning model, as described above. In this example, the second portion of the training data (e.g., the validation data) may be used to validate the predictive machine learning model.

In some non-limiting embodiments, radiological machine learning system 102 may validate the predictive machine learning model by providing validation data associated with a representation in the frequency space of an examination region of an examination object (e.g., data a representation in the frequency space of an examination region of an examination object) as input to the predictive machine learning model, and determining, based on an output of the predictive machine learning model, whether the predictive machine learning model correctly, or incorrectly, predicted a representation in the frequency space of the examination region with a specific amount of a contrast agent administered during a medical imaging technique. In some non-limiting embodiments, radiological machine learning system 102 may validate the predictive machine learning model based on a validation threshold. For example, radiological machine learning system 102 may be configured to validate the predictive machine learning model when a representation in the frequency space of the examination region with a specific amount of a contrast agent administered during a medical imaging technique (as identified by the validation data) is correctly predicted by the predictive machine learning model (e.g., when the predictive machine learning model correctly predicts 50% of a representation in the frequency space of the examination region with a specific amount of a contrast agent administered during a medical imaging technique, 70% of a representation in the frequency space of the examination region with a specific amount of a contrast agent administered during a medical imaging technique, or another threshold quantity of a representation in the frequency space of the examination region with a specific amount of a contrast agent administered during a medical imaging technique, and/or the like).

In some non-limiting embodiments, if radiological machine learning system 102 does not validate the predictive machine learning model (e.g., when a percentage of correctly predicted representation in the frequency space of the examination region with a specific amount of a contrast agent administered during a medical imaging technique does not satisfy the validation threshold), then radiological machine learning system 102 may generate one or more additional predictive machine learning models.

In some non-limiting embodiments, once the predictive machine learning model has been validated, radiological machine learning system 102 may further train the predictive machine learning model and/or generate new predictive machine learning models based on receiving new training data. The new training data may include additional data associated with one or more representations in frequency space of an examination region of an examination object. In some non-limiting embodiments, the new training data may include data associated with representations in the frequency space of an examination region of an examination object. Radiological machine learning system 102 may use the predictive machine learning model to predict a representation in the frequency space of the examination region with a specific amount of a contrast agent administered during a medical imaging technique and compare an output of the predictive machine learning model to the new training data that includes data associated with representations in the frequency space of an examination region of an examination object. In such an example, radiological machine learning system 102 may update one or more predictive machine learning models based on the new training data.

In some non-limiting embodiments, radiological machine learning system 102 may store the predictive machine learning model. For example, radiological machine learning system 102 may store the predictive machine learning model in a data structure (e.g., a database, a linked list, a tree, and/or the like). The data structure may be located within radiological machine learning system 102 or external (e.g., remote from) radiological machine learning system 102.

Figure 5A:
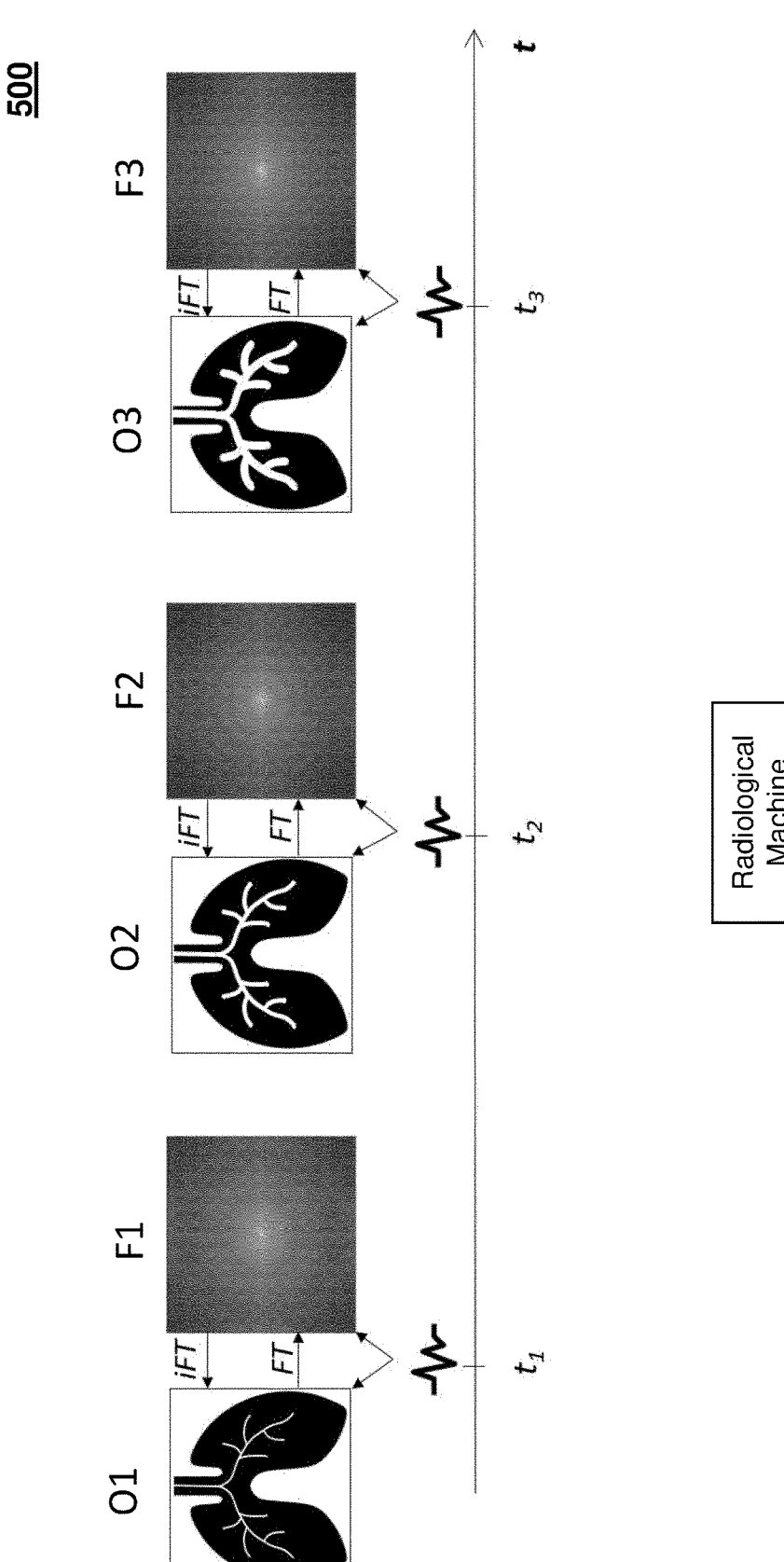
FIG. 5A is a diagram of a non-limiting embodiment of an implementation of a process for providing a prediction of a representation of an examination region that was generated using a medical image technique involving a contrast agent.
Figure 5B:
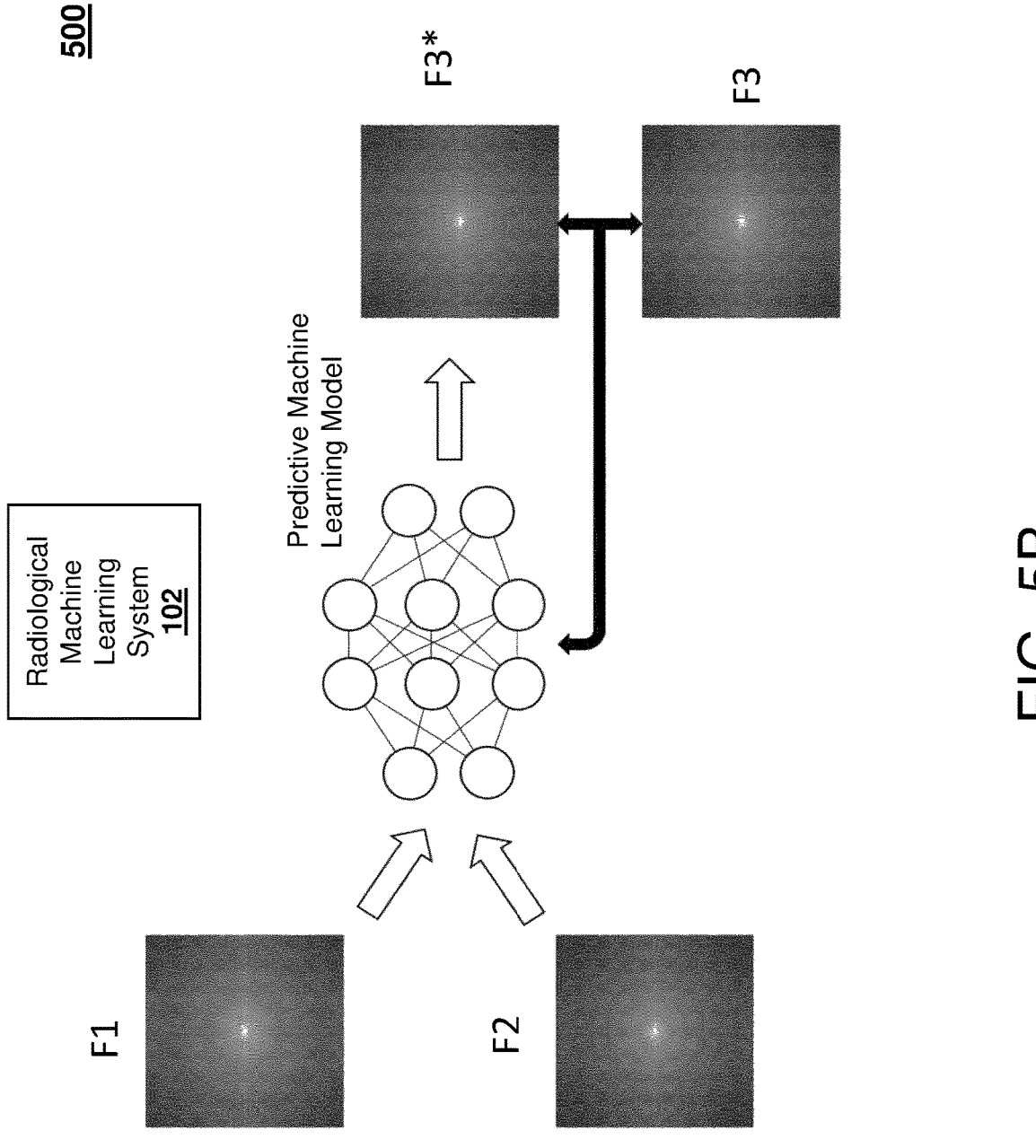
FIG. 5B is another diagram of a non-limiting embodiment of an implementation of a process for providing a prediction of a representation of an examination region that was generated using a medical image technique involving a contrast agent.
Figure 5C:
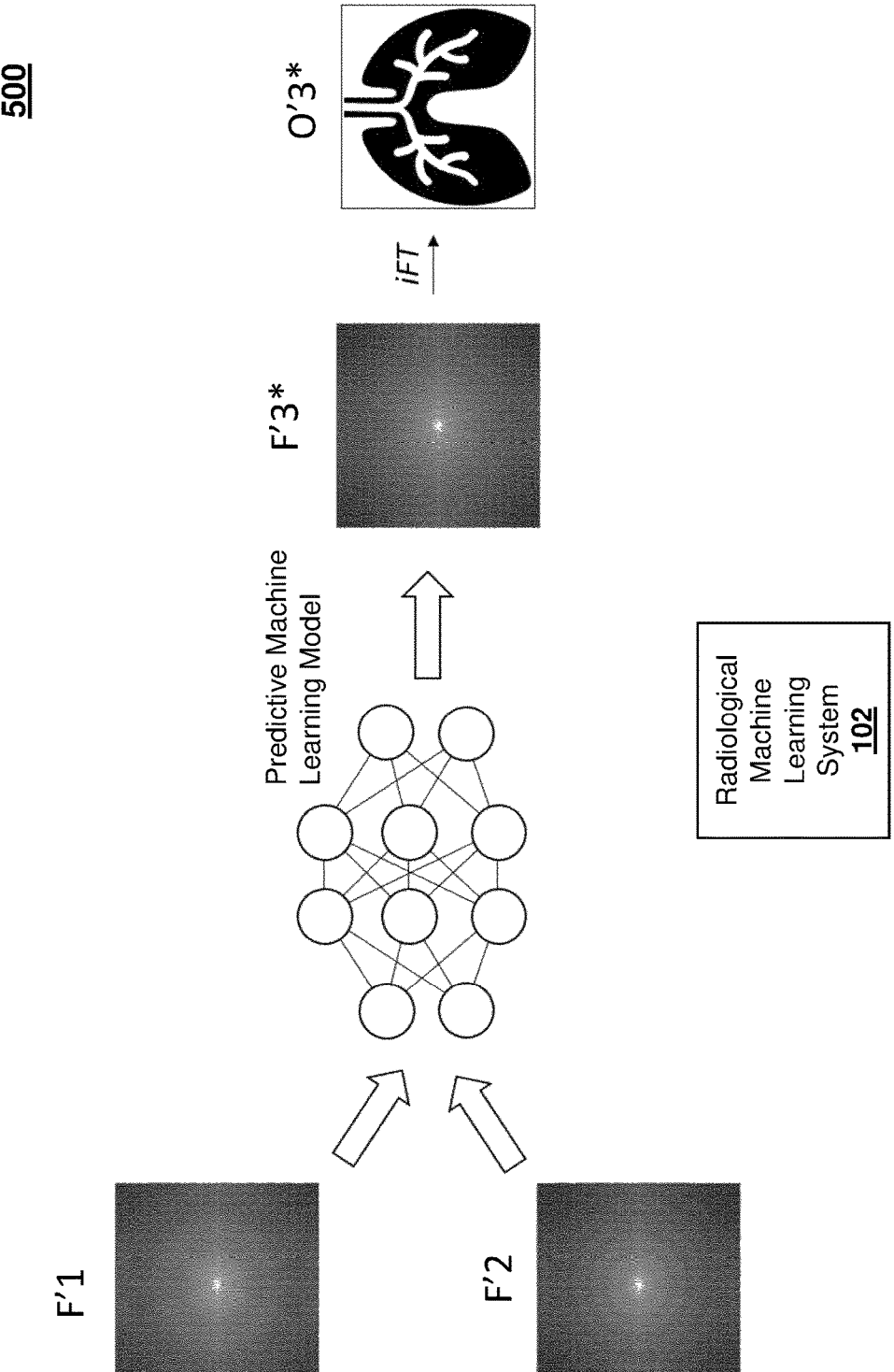
FIG. 5C is another diagram of a non-limiting embodiment of an implementation of a process for providing a prediction of a representation of an examination region that was generated using a medical image technique involving a contrast agent.

FIGS. 5A-5C show diagrams of an implementation 500 of a process (e.g., process 300) for providing a prediction of a representation of an examination region that was generated using a medical image technique involving a contrast agent. As described below with regard to FIGS. 5A-5C, implementation 500 may include radiological machine learning system 102 performing the steps of the process. In some non-limiting embodiments, one or more of the steps of the process may be performed (e.g., completely, partially, and/or the like) by another device or a group of devices separate from and/or including radiological machine learning system 102, such as medical imaging system 104 and/or user device 106.

As shown in FIG. 5A, radiological machine learning system 102 may generate representations in frequency space of an examination region of an examination object. As further shown in FIG. 5A, at three different time points t1, t2, and t3, radiological machine learning system 102 may generate three representations of an examination region of an examination object. For example, radiological machine learning system 102 may receive the results of a radiological examination that involves a medical imaging technique performed on an examination region of an examination object by medical imaging system 104. The examination region may be a lung of a human patient. The results may include three representations in real space of the examination region of the examination object based on the medical imaging technique performed on the examination region by medical imaging system 104.

The results may include three radiological images, including a first radiological image, O1, a second radiological image, O2, and a third radiological image, O3. The first radiological image, O1, may include an image of the examination region that was generated without an amount of a contrast agent administered during the medical imaging technique or with a first amount of the contrast agent administered during the medical imaging technique. The second radiological image, O2, may include an image of the examination region that was generated with a second amount of the contrast agent administered during the medical imaging technique. The third radiological image, O3, may include an image of the examination region that was generated with a third amount of the contrast agent administered during the medical imaging technique. In some non-limiting embodiments, the second amount of the contrast agent may be different from the first amount. In some non-limiting embodiments, the third amount of the contrast agent may be different from the first amount and the second amount. In one example, the first amount of the contrast agent is greater than or equal to zero, the second amount of the contrast agent is greater than the first amount of the contrast agent, and the third amount of the contrast agent is greater than the second amount of the contrast agent.

The first representation, F1, may include a representation of the examination region without an amount of a contrast agent administered during a medical imaging technique or with a first amount of the contrast agent administered during the medical imaging technique. The second representation, F2, may include a representation of the examination region with a second amount of the contrast agent administered during the medical imaging technique. The third representation, F3, may include a representation of the examination region with a third amount of the contrast agent administered during the medical imaging technique.

In some non-limiting embodiments, radiological machine learning system 102 may generate three representations in frequency space of the examination, F1, F2, and F3, of the examination object based on the results of a radiological examination performed by medical imaging system 104. For example, radiological machine learning system 102 may generate three representations in frequency space of the examination, F1, F2, and F3, based on the representations in real space of the examination region, O1, O2, and O3, using a Fourier transform (FT). The representations in real space of the examination region, O1, O2, and O3, may be converted by radiological machine learning system 102 into representations in frequency space of the examination region, F1, F2, and F3, using a FT. The representations in frequency space of the examination region, F1, F2, and F3, may be converted by radiological machine learning system 102 into the representations in real space of the examination region, O1, O2, and O3, using an inverse Fourier transform (iFT). In some non-limiting embodiments, a transform other than the FT may be used by radiological machine learning system 102 to convert representations in real space to representations in frequency space. The three main properties of such a transform may include the existence of a clear inverse transform (e.g., a clear connection between representations in real space and representations in frequency space), locality of the contrast information, and robustness with respect to deficient image registration.

As shown in FIG. 5B, representations in frequency space of the examination region, F1, F2, and F3 may be used for training a predictive machine learning model. The representations in frequency space of the examination region, F1, F2, and F3 may be included in a training data set of an examination object. Radiological machine learning system 102 may use a plurality of training data sets of a plurality of examination objects to train the predictive machine learning model.

In some non-limiting embodiments, the predictive machine learning model is trained to provide, as an output, a prediction of a representation in the frequency space of the examination region with a specific amount of the contrast agent administered during the medical imaging technique based on the first representation, F1, and the second representation, F2. In some non-limiting embodiments, the specific amount of the contrast agent corresponds to the third amount of the contrast agent administered during the medical imaging technique.

As further shown in FIG. 5B, radiological machine learning system 102 may provide an input to the predictive machine learning model and radiological machine learning system 102 may receive the output of the predictive machine learning model based on the input. In some non-limiting embodiments, the first representation, F1, and the second representation, F2, may be provided as input to the predictive machine learning model. The output of the predictive machine learning model may include a prediction of a representation in the frequency space of the examination region, F3*, with the third amount of the contrast agent administered during the medical imaging technique. As part of a training procedure, radiological machine learning system 102 may compare the prediction of the representation in the frequency space of the examination region, F3*, with the third amount of the contrast agent administered during the medical imaging technique to the third representation in the frequency space of the examination region, F3, with the third amount of the contrast agent administered during the medical imaging technique. A deviation between the prediction of the representation, F3*, and the third representation, F3, may be used in a backpropagation method to train the predictive machine learning model to reduce deviations to a defined minimum. If the predictive machine learning model has been trained on the basis of a plurality of training data sets of a plurality of examination objects and if the prediction of the representation in the frequency space of the examination region, F3*, with the third amount of the contrast agent administered during the medical imaging technique has reached a defined accuracy, the predictive machine learning model may be considered to be trained and may be used for prediction.

As shown in FIG. 5C, radiological machine learning system 102 may use the predictive machine learning model to provide a prediction of a representation in the frequency space of an examination region of an examination object with a specific amount of the contrast agent administered during a medical imaging technique. In some non-limiting embodiments, radiological machine learning system 102 may receive a first representation in frequency space, F'1, of an examination region of an examination object. The first representation in frequency space, F'1, may include a representation of the examination region without an amount of a contrast agent administered during a medical imaging technique or with a first amount of the contrast agent administered during a medical imaging technique. In some non-limiting embodiments, radiological machine learning system 102 may receive a second representation in the frequency space, F'2, of the examination region of the examination object. In some non-limiting embodiments, the second representation in the frequency space, F'2, may include a representation of the examination region with a second amount of the contrast agent administered during the medical imaging technique and the second amount of the contrast agent may be greater than the first amount of the contrast agent.

As further shown in FIG. 5C, radiological machine learning system 102 may provide an input to a predictive machine learning model. The input to the predictive machine learning model may include the first representation in frequency space, F'1, and the second representation in the frequency space, F'2. The predictive machine learning model may include a trained machine learning model that is configured to provide, as an output, a prediction of a representation in the frequency space, F'3*, of the examination region with a third amount of the contrast agent administered during the medical imaging technique. In some non-limiting embodiments, the third amount of the contrast agent is greater than the first amount of the contrast agent and the second amount of the contrast agent.

As further shown in FIG. 5C, radiological machine learning system 102 may receive the output, F'3*, of the predictive machine learning model based on the input and convert the output of the predictive machine learning model to a predicted representation in real space, O'3*, of the examination region of the examination object using an iFT. In some non-limiting embodiments, radiological machine learning system 102 may provide the predicted representation in the real space, O'3*, of the examination region of the examination object.

Figure 6A:
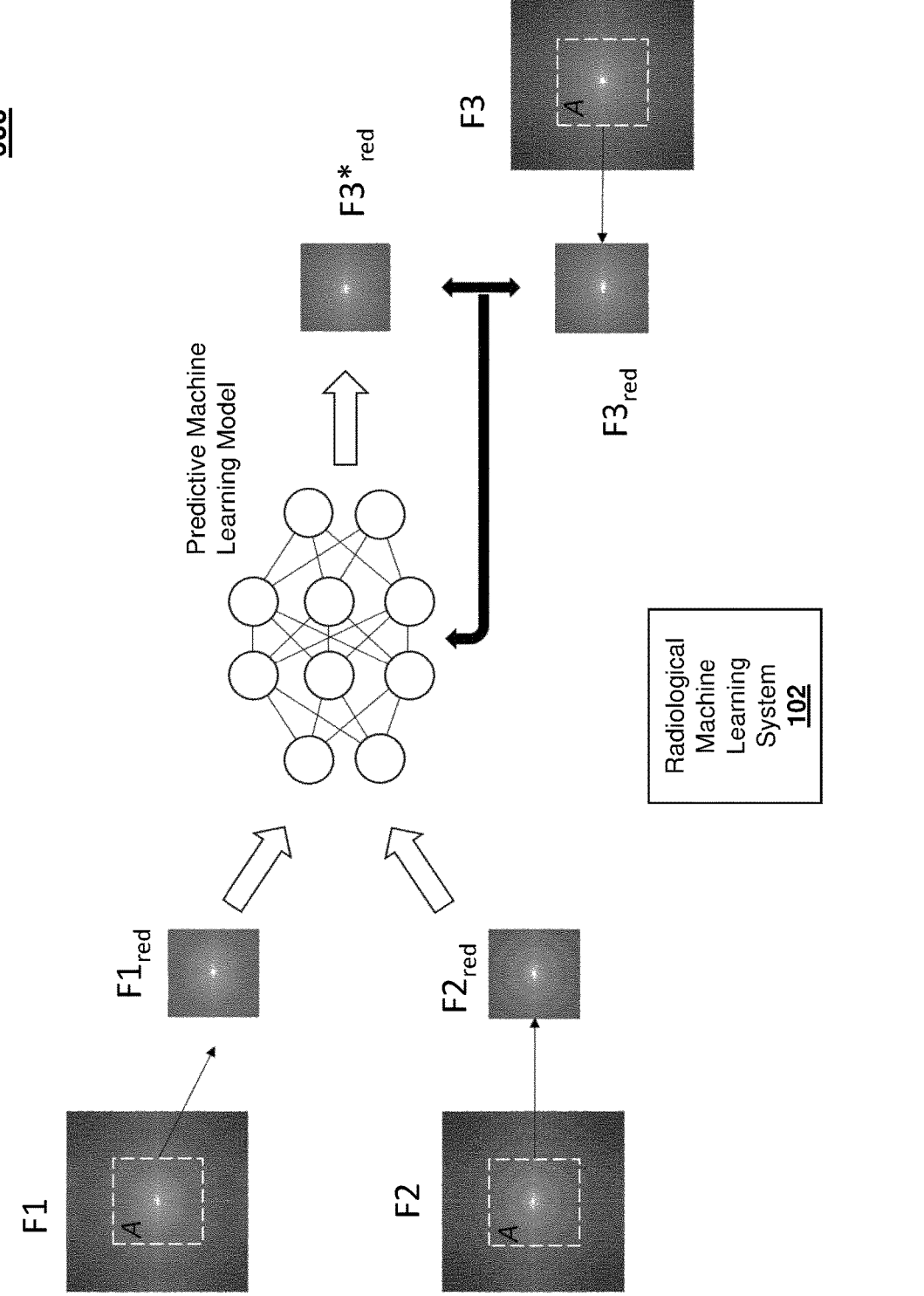
FIG. 6A is a diagram of a non-limiting embodiment of an implementation of a process for providing a prediction of a representation of an examination region that was generated using a medical image technique involving a contrast agent.
Figure 6B:
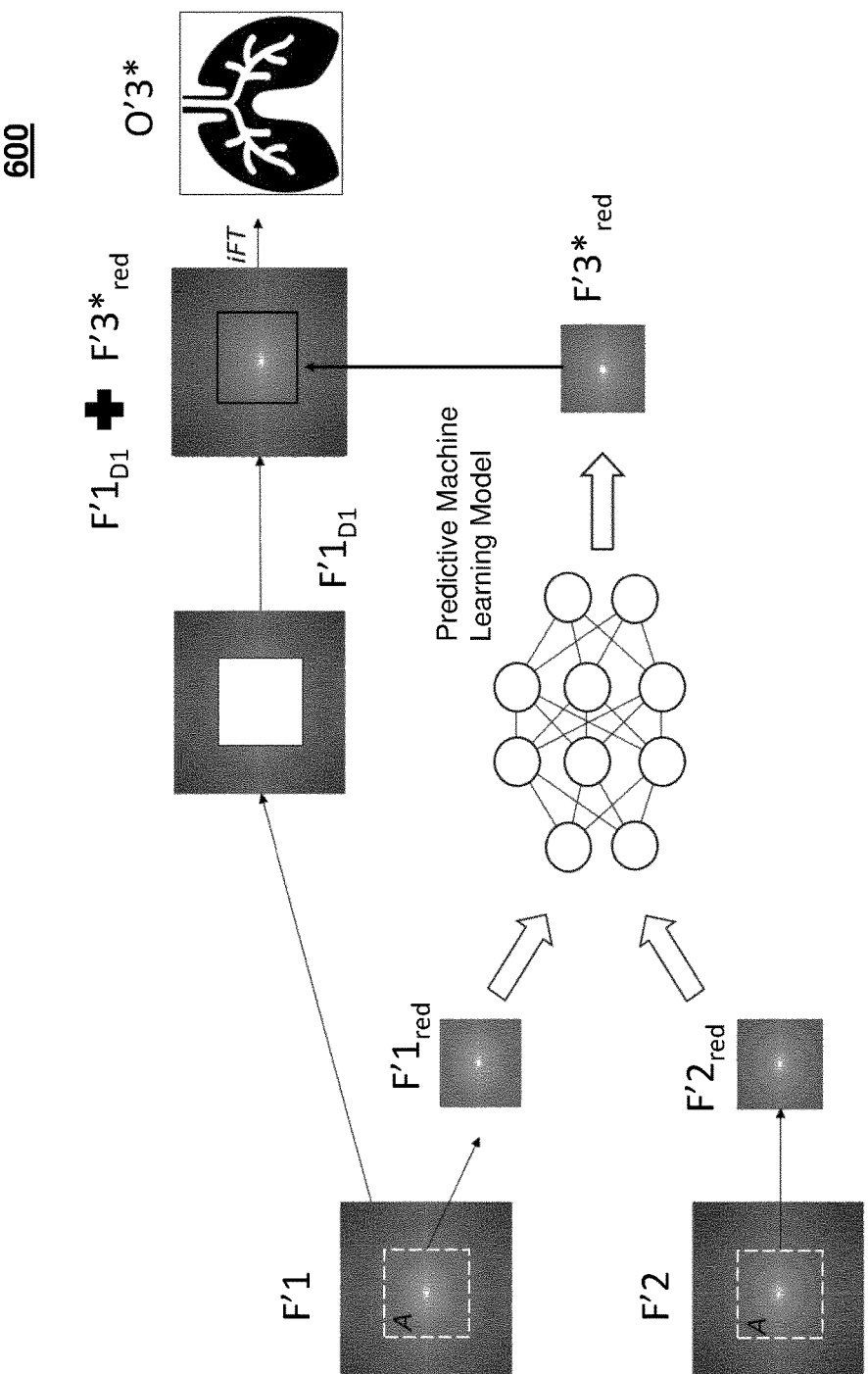
FIG. 6B is another diagram of a non-limiting embodiment of an implementation of a process for providing a prediction of a representation of an examination region that was generated using a medical image technique involving a contrast agent.

FIGS. 6A-6B show diagrams of an implementation 600 of a process (e.g., process 300) for providing a prediction of a representation of an examination region that was generated using a medical image technique involving a contrast agent. As described below with regard to FIGS. 6A-6B, implementation 600 may include radiological machine learning system 102 performing the steps of the process. In some non-limiting embodiments, one or more of the steps of the process may be performed (e.g., completely, partially, and/or the like) by another device or a group of devices separate from and/or including radiological machine learning system 102, such as medical imaging system 104 and/or user device 106.

As shown in FIG. 6A, in a same or similar fashion as with implementation 500, representations in frequency space of the examination region, F1, F2, and F3, may be used for training a predictive machine learning model. The representations in frequency space of the examination region, F1, F2, and F3 may be included in a training data set of an examination object. Radiological machine learning system 102 may use a plurality of training data sets of a plurality of examination objects to train the predictive machine learning model.

As with implementation 500, the first representation, F1, may include a representation of the examination region without an amount of a contrast agent administered during a medical imaging technique or with a first amount of the contrast agent administered during the medical imaging technique, the second representation, F2, may include a representation of the examination region with a second amount of the contrast agent administered during the medical imaging technique, and the third representation, F3, may include a representation of the examination region with a third amount of the contrast agent administered during the medical imaging technique.

In some non-limiting embodiments, in a same or similar fashion as with implementation 500, radiological machine learning system 102 may generate three representations in frequency space, F1, F2, and F3, of the examination region of the examination object based on the results of a radiological examination performed by medical imaging system 104. In some non-limiting embodiments, the predictive machine learning model is trained to provide, as an output, a prediction of a portion of a representation in the frequency space of the examination region with a specific amount of the contrast agent administered during the medical imaging technique based on a portion of the first representation and a portion of the second representation. In some non-limiting embodiments, the specific amount of the contrast agent corresponds to the third amount of the contrast agent administered during the medical imaging technique.

As further shown in FIG. 6A, radiological machine learning system 102 may specify a portion, A, of the first representation, F1, that includes a center of the frequency space to provide a first reduced representation in the frequency space, F1red, of the examination region of the examination object. Additionally, radiological machine learning system 102 may specify a portion, A, of the second representation, F2, that includes a center of the frequency space to provide a second reduced representation in the frequency space, F2red, of the examination region of the examination object. Additionally, radiological machine learning system 102 may specify a portion, A, of the third representation, F3, that includes a center of the frequency space to provide a third reduced representation in the frequency space, F3red, of the examination region of the examination object.

As further shown in FIG. 6A, radiological machine learning system 102 may provide first reduced representation in the frequency space, F1red, of the examination region of the examination object and the second reduced representation in the frequency space, F2red, of the examination region of the examination object as the input to the predictive machine learning model, and radiological machine learning system 102 may receive the output of the predictive machine learning model based on the input. In some non-limiting embodiments, the output may include the prediction of the portion of the representation in the frequency space, F3*red, of the examination region with the third amount of the contrast agent administered during the medical imaging technique.

As part of a training procedure, radiological machine learning system 102 may compare the prediction of the portion of the representation in the frequency space, F3*red, of the examination region with the third amount of the contrast agent administered during the medical imaging technique to the third reduced representation in the frequency space, F3red, of the examination region of the examination object. A deviation between the prediction of the portion of the representation in the frequency space, F3*red, and the third reduced representation in the frequency space, F3red, may be used in a backpropagation method to train the predictive machine learning model to reduce deviations to a defined minimum. If the predictive machine learning model has been trained on the basis of a plurality of training data sets of a plurality of examination objects and if the prediction of the portion of the representation in the frequency space, F3*red, with the third amount of the contrast agent administered during the medical imaging technique has reached a defined accuracy, the predictive machine learning model may be considered to be trained and may be used for prediction.

As shown in FIG. 6B, radiological machine learning system 102 may use the predictive machine learning model to provide a prediction of a representation in the frequency space of an examination region of an examination object with a specific amount of contrast agent administered during a medical imaging technique. In some non-limiting embodiments, radiological machine learning system 102 may receive a first representation in frequency space, F'1, of an examination region of an examination object. The first representation in frequency space, F'1, may include a representation of the examination region without an amount of a contrast agent administered during a medical imaging technique or with a first amount of the contrast agent administered during a medical imaging technique. In some non-limiting embodiments, radiological machine learning system 102 may receive a second representation in the frequency space, F'2, of the examination region of the examination object. In some non-limiting embodiments, the second representation in the frequency space, F'2, may include a representation of the examination region with a second amount of the contrast agent administered during the medical imaging technique, and the second amount of the contrast agent may be greater than the first amount of the contrast agent.

As further shown in FIG. 6B, radiological machine learning system 102 may specify a portion, A, of the first representation, F'1, that includes a center of the frequency space to provide a first reduced representation in the frequency space, F'1red, of the examination region of the examination object. Additionally, radiological machine learning system 102 may specify a portion, A, of the second representation, F'2, that includes a center of the frequency space to provide a second reduced representation in the frequency space, F'2red, of the examination region of the examination object.

As further shown in FIG. 6B, radiological machine learning system 102 may provide an input to a predictive machine learning model. The input to the predictive machine learning model may include the first reduced representation in frequency space, F'1red, and the second reduced representation in the frequency space, F'2red. The predictive machine learning model may include a trained machine learning model that is configured to provide, as an output, a prediction of a reduced representation in the frequency space, F'3\*red, of the examination region with a third amount of the contrast agent administered during the medical imaging technique. In some non-limiting embodiments, the third amount of the contrast agent is greater than the first amount of the contrast agent and the second amount of the contrast agent.

As further shown in FIG. 6B, radiological machine learning system 102 may receive the output, F'3\*red, of the predictive machine learning model based on the input and radiological machine learning system 102 may supplement the output of the predictive machine learning model, F'3\*red, with a portion of the first representation, F'1D1, that does not include the center of the frequency space and was not specified to provide the first reduced representation in the frequency space, F'1red, of the examination region of the examination object, to provide a supplemented output of the predictive machine learning model, F'1D1+F'3\*red. In some non-limiting embodiments, radiological machine learning system 102 may convert the supplemented output of the predictive machine learning model to a predicted representation in real space, O'3\*, of the examination region of the examination object using an iFT. In some non-limiting embodiments, radiological machine learning system 102 may provide the predicted representation in the real space, O'3\*, of the examination region of the examination object.

Although the above systems, methods, and computer program products have been described in detail for the purpose of illustration based on what is currently considered to be the most practical and preferred embodiments or aspects, it is to be understood that such detail is solely for that purpose and that the present disclosure is not limited to the described embodiments or aspects but, on the contrary, is intended to cover modifications and equivalent arrangements that are within the spirit and scope of the appended claims. For example, it is to be understood that the present disclosure contemplates that, to the extent possible, at least one feature of any embodiment or aspect can be combined with at least one feature of any other embodiment or aspect.

What is claimed is:

1. A method for providing a prediction of a representation of an examination region that was generated using a medical image technique involving a contrast agent, the method comprising:

administering a first amount of the contrast agent to a patient;

receiving, from a magnetic resonance imaging (MRI) machine, a first representation in frequency space of an examination region of the patient, wherein the first representation comprises a representation of the examination region with the first amount of the contrast agent administered during the medical imaging technique;

administering a second amount of contrast agent to the patient;

receiving, from the MRI machine, a second representation in the frequency space of the examination region of the patient, wherein the second representation represents the examination region with the second amount of the contrast agent administered during the medical imaging technique, wherein the second amount of the contrast agent is different from the first amount of the contrast agent;

providing an input to a predictive machine learning model, wherein the input to the predictive machine learning model comprises at least a portion of the first representation and at least a portion of the second representation, wherein the predictive machine learning model comprises a trained machine learning model configured to provide, as an output, a prediction of a representation in the frequency space of the examination region after hypothetical administration of a third amount of the contrast agent, wherein the third amount of the contrast agent is greater than each of the first amount of the contrast agent and the second amount of the contrast agent;

training the predictive machine learning model based on a training data set, wherein the training data set comprises:

a set of reference representations in the frequency space of an examination region for each examination object of a plurality of examination objects, wherein the set of reference representations comprises:

a first reference representation in the frequency space of the examination region of the examination object;

a second reference representation in the frequency space of the examination region of the examination object;

and a third reference representation in the frequency space of the examination region of the examination object; and wherein the first reference representation comprises a reference representation in the frequency space of the examination region with a first amount of the contrast agent administered during a medical imaging technique;

wherein the second reference representation comprises a reference representation in the frequency space of the examination region with a second amount of the contrast agent administered during the medical imaging technique; and wherein the third reference representation comprises a reference representation in the frequency space of the examination region with a third amount of the contrast agent administered during the medical imaging technique;

receiving the output of the predictive machine learning model based on the input;

converting the output of the predictive machine learning model to a predicted representation comprising an artificial image in real space of the examination region of the patient; and displaying the artificial image on a display.

2. The method of claim 1, further comprising:

specifying the portion of the first representation to include a center of the frequency space, specifying the portion of the second representation to include the center of the frequency space, or the portion of the first representation and the portion of the second representation to each include the center of the frequency space, to provide a reduced representation in the frequency space of the examination region of the patient, wherein the input to the predictive machine learning model comprises the reduced representation in the frequency space of the examination region of the patient; and wherein providing the input to the predictive machine learning model comprises providing the reduced representation in the frequency space of the examination region of the patient as the input to the predictive machine learning model.

3. The method of claim 2, further comprising:

supplementing the output of the predictive machine learning model with:

another portion of the first representation that does not include the center of the frequency space and was not specified to provide the reduced representation in the frequency space of the examination region of the patient, another portion of the second representation that does not include the center of the frequency space and was not specified to provide the reduced representation in the frequency space of the examination region of the patient, or another portion of the first representation and another portion of the second representation, each of which do not include the center of the frequency space and were not specified to provide the reduced representation in the frequency space of the examination region of the patient; and providing a supplemented output of the predictive machine learning model;

wherein converting the output of the predictive machine learning model to the predicted representation in the real space of the examination region of the patient comprises converting the supplemented output of the predictive machine learning model to the predicted representation in the real space of the examination region of the patient.

4. The method of claim 1, wherein the second amount of contrast agent administered during the medical imaging technique is greater than the first amount of contrast agent.

5. The method of claim 1, wherein receiving the first representation in the frequency space of the examination region of the patient comprises receiving first k-space data associated with the examination region of the patient, and receiving the second representation in the frequency space of the examination region of the patient comprises receiving second k-space data associated with the examination region of the patient.

6. The method of claim 1, wherein training the predictive machine learning model comprises:

minimizing an amount of error provided by an error function, wherein the error function quantifies a deviation between a prediction of a representation in the frequency space of the examination region of the examination object with the third amount of the contrast agent administered during the medical imaging technique and the third reference representation in the frequency space of the examination region of the examination object.

7. The method of claim 1, further comprising:

training the predictive machine learning model based on a training data set, wherein the training data set comprises:

a set of reduced reference representations in the frequency space of an examination region for each examination object of a plurality of examination objects, each set of reduced reference representations comprising:

a first reduced reference representation in the frequency space of the examination region of the examination object;

a second reduced reference representation in the frequency space of the examination region of the examination object; and a third reduced reference representation in the frequency space of the examination region of the examination object; and wherein the first reduced reference representation comprises a reference representation of a portion of a first reference representation in the frequency space of the examination region that includes a center of the frequency space, wherein the first reference representation comprises a reference representation of the examination region with the first amount of the contrast agent administered during a medical imaging technique;

wherein the second reduced reference representation comprises a reference representation of a portion of a second reference representation in the frequency space of the examination region that includes a center of the frequency space, wherein the second reference representation comprises a reference representation of the examination region with the second amount of the contrast agent administered during the medical imaging technique; and wherein the third reduced reference representation comprises a reference representation of a portion of a third reference representation in the frequency space of the examination region that includes a center of the frequency space, wherein the third reference representation comprises a reference representation of the examination region with the third amount of the contrast agent administered during the medical imaging technique.

8. The method of claim 7, wherein training the predictive machine learning model comprises minimizing an amount of error provided by an error function, wherein the error function quantifies a deviation between a prediction of a reduced representation in the frequency space of the examination region of the examination object with the third amount of the contrast agent administered during the medical imaging technique and the third reduced reference representation in the frequency space of the examination region of the examination object.

\* \* \* \* \*